(12) United States Patent
Wright et al.

(10) Patent No.: US 11,975,154 B2
(45) Date of Patent: May 7, 2024

(54) RESPIRATORY DEVICE

(71) Applicant: Fisher & Paykel Healthcare Limited, Auckland (NZ)

(72) Inventors: Douglas Richard Wright, Auckland (NZ); Peter Lawrence Grylls, Auckland (NZ); Andrew Paul Maxwell Salmon, Auckland (NZ); Philip John Dickinson, Auckland (NZ); Yi-Cheng Sun, Auckland (NZ); Silvan Terence Butler, Auckland (NZ); Sergiu Constantin Filip, Auckland (NZ); Samuel William Saunders, Auckland (NZ); Andrew Martin Letton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 220 days.

(21) Appl. No.: 17/305,271

(22) Filed: Jul. 2, 2021

(65) Prior Publication Data
US 2021/0346635 A1    Nov. 11, 2021

Related U.S. Application Data

(63) Continuation of application No. 16/310,798, filed as application No. PCT/NZ2017/050084 on Jun. 16, 2017, now Pat. No. 11,083,866.
(Continued)

(51) Int. Cl.
*A61M 16/16* (2006.01)
*A61M 16/00* (2006.01)
*A61M 16/10* (2006.01)

(52) U.S. Cl.
CPC ........ *A61M 16/16* (2013.01); *A61M 16/0066* (2013.01); *A61M 16/0087* (2013.01);
(Continued)

(58) Field of Classification Search
CPC .............. A61M 16/00; A61M 16/0057; A61M 16/0066; A61M 16/022; A61M 16/024;
(Continued)

(56) References Cited

U.S. PATENT DOCUMENTS

| 3,243,100 A | 3/1966 | Adams |
|---|---|---|
| 3,659,604 A | 5/1972 | Melville et al. |

(Continued)

FOREIGN PATENT DOCUMENTS

| EP | 2055340 | 5/2009 |
|---|---|---|
| JP | 2003-103578 | 4/2003 |

(Continued)

OTHER PUBLICATIONS

International Search Report, PCT/NZ2017/050084, dated Aug. 23, 2017, in 12 pages.

*Primary Examiner* — Joseph D. Boecker
(74) *Attorney, Agent, or Firm* — Knobbe, Martens, Olson & Bear, LLP

(57) ABSTRACT

The invention relates to a breathing assistance apparatus that may be configured to reduce the risk of damage to electronics within the apparatus as a result of liquid leaks within the apparatus or impacts to the apparatus. In other forms, the apparatus may be configured to allow for easy assembly and/or safe operation.

20 Claims, 15 Drawing Sheets

Related U.S. Application Data

(60) Provisional application No. 62/357,807, filed on Jul. 1, 2016.

(52) U.S. Cl.
CPC ........ *A61M 16/109* (2014.02); *A61M 16/161* (2014.02); *A61M 16/024* (2017.08); *A61M 2205/3368* (2013.01); *A61M 2205/3372* (2013.01); *A61M 2205/3606* (2013.01); *A61M 2205/502* (2013.01)

(58) Field of Classification Search
CPC .. A61M 16/109; A61M 16/16; A61M 16/161; A61M 2205/3606; A61M 2205/502; A61M 2205/505; F24F 2006/008; F24F 6/025; F24F 6/10
See application file for complete search history.

(56) References Cited

U.S. PATENT DOCUMENTS

| | | | |
|---|---|---|---|
| 4,028,444 A | 6/1977 | Brown et al. | |
| 4,597,917 A * | 7/1986 | Lunsford | A61M 16/1075 261/153 |
| 4,682,010 A | 7/1987 | Drapeau et al. | |
| 4,807,616 A * | 2/1989 | Adahan | A61M 16/0069 417/44.1 |
| 6,954,329 B1 | 10/2005 | Ojeda et al. | |
| 11,083,866 B2 | 8/2021 | Wright et al. | |
| 2009/0107493 A1 | 4/2009 | Liu et al. | |
| 2009/0107982 A1 | 4/2009 | McGhin et al. | |
| 2010/0065051 A1* | 3/2010 | Potharaju | A61M 16/0816 128/203.26 |
| 2013/0174843 A1* | 7/2013 | Smith | A61M 16/1075 128/203.26 |
| 2014/0116433 A1 | 5/2014 | Ghalib et al. | |
| 2014/0216459 A1 | 8/2014 | Vos et al. | |
| 2015/0202402 A1* | 7/2015 | Kat | A61M 16/109 128/203.27 |
| 2016/0101256 A1 | 4/2016 | Potharaju et al. | |
| 2016/0375216 A1 | 12/2016 | Sun | |

FOREIGN PATENT DOCUMENTS

| | | | | |
|---|---|---|---|---|
| WO | WO-2015025264 A1 * | 2/2015 | ............ | A61M 16/00 |
| WO | WO 2015/038013 | 3/2015 | | |

* cited by examiner

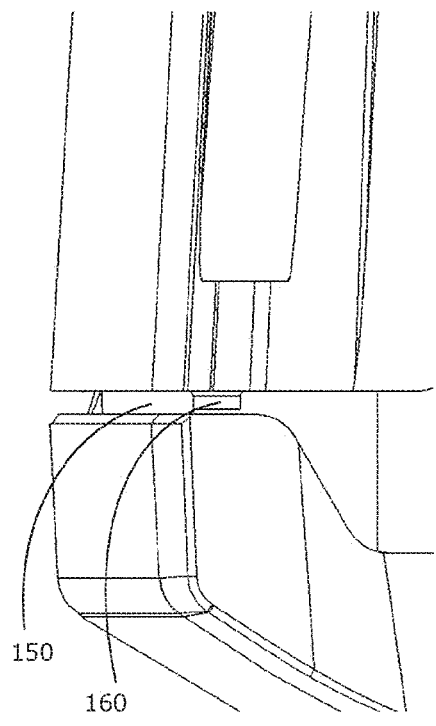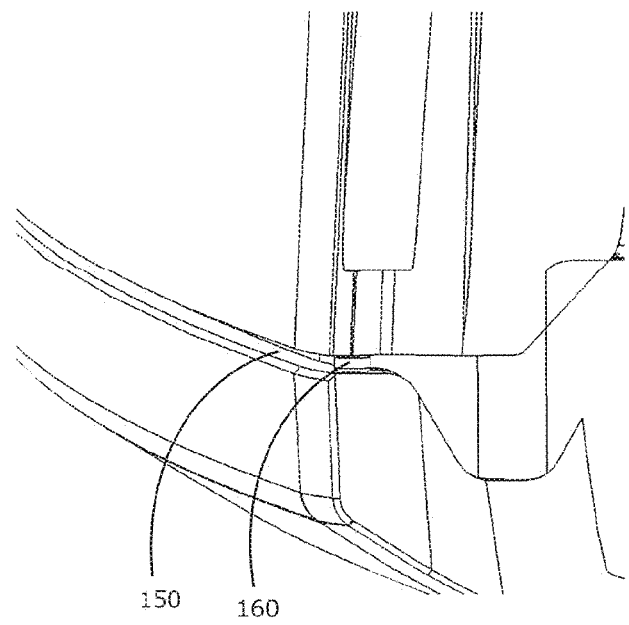
Figure 19a
Figure 19b

RESPIRATORY DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

*Field of the Invention*

The present invention generally relates to respiratory devices. More particularly, the present invention relates to respiratory devices for humidifying breathing gases.

*Description of the Related Art*

Breathing treatment devices typically include an airflow generator to supply pressurized breathing gases. In some breathing treatment devices, an integrated water supply chamber may be provided. The water chamber can include a supply of water that is used to humidify the breathing gases that are being supplied by the breathing treatment device.

In some configurations, the breathing treatment devices are designed to be portable and/or movable. When such devices are moved while containing water in a water supply reservoir, the reservoir may tip and allow water to spill from the water reservoir into other regions of the breathing treatment devices. Where the device is formed of many separate parts, there is a risk that water could seep between parts and damage electronic components within the device.

In some configurations, the breathing treatment devices may comprise one or more sensors at various locations within the device, which may make it difficult to service these sensors.

The present invention may go at least some way towards reducing the risk that electronic components within a breathing treatment device, such as a CPAP machine, may be damaged as a result of liquid leaking into the device.

SUMMARY OF THE INVENTION

CPAP machines include an airflow generator to supply pressurized gas to a user. Many CPAP machines include a heated water bath or other source of water for humidification of the pressurized gas. CPAP machines are often used in bedrooms or other sleeping quarters and are placed on nightstands, for example. As such, it may be desirable for the CPAP machine to look aesthetically pleasing. It may also be desirable for the CPAP machine to be substantially stable when placed on a supporting surface, such as on a nightstand. It may also be desirable for CPAP machines to be easily refilled with water, and to be moved when containing water, with minimum risk of spills that may cause water damage to the sensitive electronic components within the machine. CPAP machines may also need to be serviced from time to time and so it may be useful for the key components of the machine to be readily accessible for servicing.

In one aspect, the invention provides a breathing assistance apparatus for the delivery of breathing gas to a user, wherein the apparatus comprises a body and a lid, wherein the body comprises at least one housing comprising at least one outer wall; at least one inner wall substantially adjacent to and spaced apart from the outer wall; and an upper surface spanning between upper edges of the at least one outer and inner wall, wherein the outer and inner walls and upper surface are integrally formed as one part.

Preferably, the inner wall forms an enclosure for a humidification chamber, and the lid covers the enclosure. Optionally, a heating element is located in an aperture of the lower wall of the enclosure.

In one form, the outer and inner walls may be formed without seams or joins. In one form, the breathing assistance apparatus may comprise four inner walls and three outer walls, wherein the three outer walls are located substantially adjacent to and spaced apart from three of the four inner walls. A face plate may be located substantially adjacent to the remaining inner wall. The face plate may comprise a user interface through which a user may control the apparatus.

Preferably, the body of the at least one housing comprises three inner walls and three outer walls, each outer wall being substantially adjacent to and spaced apart from a respective one of the three inner walls; and wherein the housing further comprises a fourth inner wall and a face plate located substantially adjacent to and spaced apart from the fourth inner wall to form an outer wall of the housing. Optionally, substantially the whole of the face plate is tinted.

In one form, the apparatus further comprises a printed circuit board (PCB) located within the at least one housing and positioned behind the face plate, wherein the apparatus further comprises a compressible facing comprising a first portion located between the PCB and face plate and a second portion located between the PCB and interior structures of the housing to provide damping to both faces of the PCB. Preferably, the PCB comprises one or more apertures through which arms of the compressible facing may project so that the PCB is supported by the compressible facing. Optionally, the first portion of the compressible facing comprises one or more apertures that substantially align with LED lit components located on the PCB.

In one form, the apparatus comprises an upper housing, a lower housing and a base, wherein the lower housing is connected to both the upper housing and the base, and wherein the face plate forms an outer wall for at least the upper housing and lower housing.

In one form, the apparatus comprises two or more sensors located on one face of the PCB and wherein the apparatus further comprises an interior wall comprising two or more apertures that substantially align with the sensors, such that the sensors may be caused to project through the apertures in the interior wall and into an air flow path located within the apparatus, by pushing the PCB against interior wall. Optionally, the apertures comprise soft seals around walls of the apertures and the soft seals are co-molded to the interior wall of the apparatus.

In another aspect, the invention provides a breathing assistance apparatus for the delivery of breathing gas to a user, wherein the apparatus comprises two or more sensors located on one face of a PCB and wherein the apparatus further comprises an interior wall comprising two or more apertures that substantially align with the sensors, such that the sensors may be caused to project through the apertures in the interior wall and into an air flow path located within the apparatus, by pushing the PCB against interior wall. Preferably, the interior wall is a wall of an air flow path. In this form, the sensors may project through apertures in the interior wall and into the air flow path.

Preferably, the apertures comprise soft seals around walls of the apertures and the soft seals are co-molded to the interior wall of the apparatus.

In yet another aspect, the invention provides a breathing assistance apparatus for the delivery of breathing gas to a user, wherein the apparatus comprises: a heating element for heating a humidification chamber; a control system comprising a first electronic protection circuit connected to the heating element and comprising: a first temperature sensor configured to sense the temperature of the heating element and produce outputs based on the sensed temperature; a first comparator circuit; a first switching member; and a programmable control unit; wherein the first comparator circuit is configured to receive outputs from the first temperature sensor and compare those outputs with a first predetermined temperature threshold T1 to determine if the heater plate temperature exceeds the first predetermined temperature threshold T1 and to cause the first switching member to disable power to the heating element when the sensed heating element temperature exceeds the first predetermined threshold temperature T1 and wherein the programmable control unit is configured to receive outputs from the first temperature sensor and to cause the first switching member to disable power to the heating element when the sensed heating element temperature exceeds a first predetermined programmed threshold temperature, which may be equal to or greater than T1.

Optionally, the first switching member is an electronically controlled switch configured to disable power to the heating element by electronically breaking the electronic circuit to the heating element.

Alternatively, the first switching member is an electronically controlled moveable switch configured to disable power to the heating element by moving from a first position to a second position to physically break the electronic circuit to the heating element.

In one form, the control system further comprises: a second electronic protection circuit comprising: a second temperature sensor configured to sense the temperature of the heating element and produce outputs based on the sensed temperature; a second comparator circuit; and a second switching member wherein the second comparator circuit is configured to receive outputs from the second temperature sensor and compare those outputs with a second predetermined threshold temperature T2 to determine if the heater plate temperature exceeds the second predetermined temperature threshold T2 and to cause the second switching member to disable power to the heating element when the sensed heating element temperature exceeds the second predetermined threshold temperature T2, which may be equal to or greater than T1.

Optionally, the programmable control unit is configured to receive temperature outputs from the second temperature sensor and to cause the second switching member to disable power to the heating element when the sensed heating element temperature exceeds a second predetermined programmed threshold temperature, which may be equal to or greater than T2.

In one form, the programmable control unit is configured to receive outputs from the first and second temperature sensors and calculate a control unit sensed temperature by averaging the outputs of the first and second temperature sensors and to then compare the control unit sensed temperature to the first predetermined programmed temperature and to the second predetermined programmed temperature and cause the first or second switching member to disable power to the heating element if the control unit sensed temperature exceeds of the first or second predetermined programmed temperatures.

In one form, the control unit is configured to cause the switching member(s) to disable power to the heating element if the control unit sensed temperature exceeds the first or second predetermined programmed temperature threshold for a predetermined period of time.

In one form, the second switching member is an electronically controlled moveable switch configured to disable power to the heating element by moving from a first position to a second position to physically break the electronic circuit to the heating element.

In one form, the control unit is configured to identify the difference in outputs of the first and second temperature sensors and to cause the switching member(s) to disable power to the heating element when the control unit identifies that the outputs of the first and second temperature sensors differ by a predetermined threshold.

In yet another aspect, the invention provides a method of manufacturing a plastic housing for the breathing assistance apparatus of the invention and comprising the step of injection moulding the plastic housing by configuring an injection moulding machine so that its gates are located at diametrically opposed corners of the upper surface of the housing.

Because of the cramped spaces in which CPAP machines are used, easy manipulation of a lid or other component used to enclose a water reservoir or the like is desired. Preferably, the lid or other such component can be easily pivoted about hinges.

Moreover, to improve the ability to access the water reservoir, the lid preferably carries a locking mechanism that is configured to allow a user to release the lock and open the lid with a single hand, preferably, with the single hand in a single position. Such configurations are a welcomed improvement over configurations requiring one hand to operate the lock and another hand to subsequently raise the lid.

BRIEF DESCRIPTION OF THE DRAWINGS

These and other features, aspects and advantages of the present invention will be described with reference to preferred embodiments shown in the following drawings, in which:

FIG. 19a is a side view showing part of the join between the upper and lower housings;

FIG. 19b is another side view showing part of the join between the upper and lower housings;

DETAILED DESCRIPTION OF THE PREFERRED EMBODIMENTS

Figure 1:
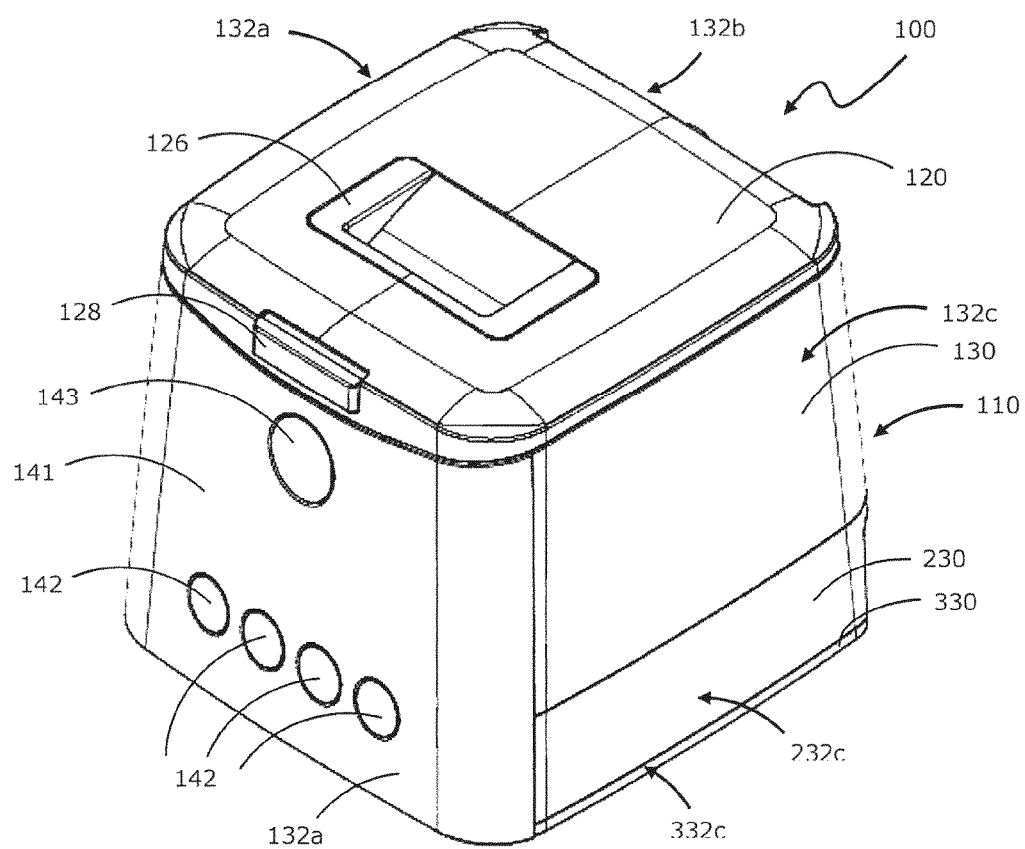
FIG. 1 is a perspective view of one form of breathing assistance apparatus according to the invention.
Figure 2:
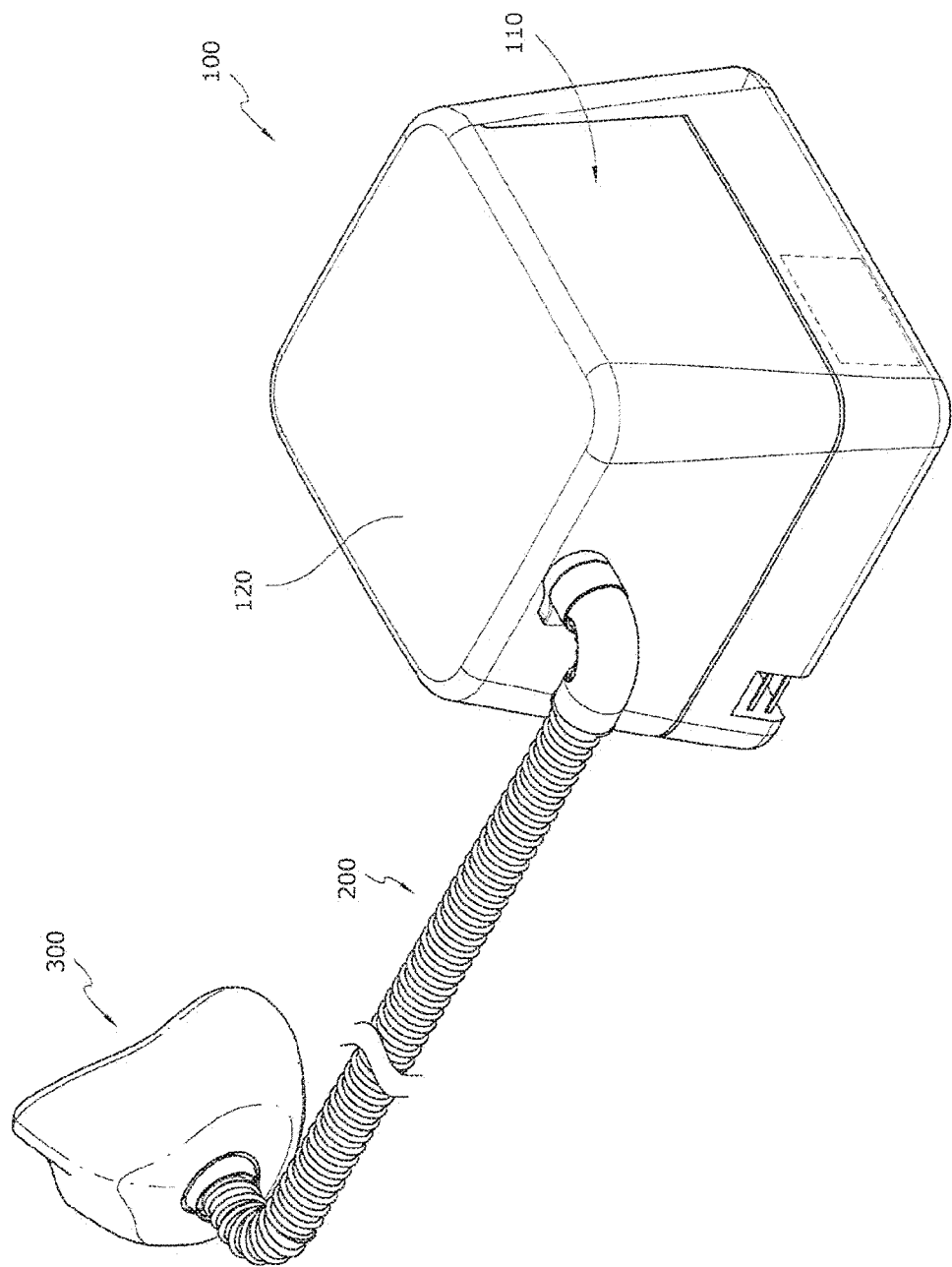
FIG. 2 is a perspective view of the breathing assistance apparatus of FIG. 1 when attached to a breathing tube and an interfacing structure

FIG. 1 illustrates a breathing assistance apparatus 100 that is arranged and configured in accordance with certain features, aspects and advantages of the present invention. FIG. 2 shows one form of breathing assistance apparatus 100 connected to a breathing tube 200 and an interfacing structure 300. In the embodiment illustrated, the interfacing structure 300 is a mask, but the breathing assistance apparatus 100 of the invention may be used with any suitable form of interfacing structure, including a nasal cannula or nasal pillows, for example.

In one form, as shown in FIGS. 1 to 21, the breathing apparatus 100 is a CPAP machine that includes a housing comprising a body 110 and a lid 120. The body 110 may be configured to house a humidification chamber with water reservoir, a heating element, a blower, and an electronic system that connects a user interface to electronic components of the CPAP machine 100.

In one form, as shown in FIG. 1, the body 110 may comprise an upper housing 130, a lower housing 230 positioned beneath the upper housing 130, and a base 330 positioned beneath the lower housing 230.

The upper housing 130 may be configured to house a humidification chamber. In one form, the upper housing 130 comprises heating element that, in use, contacts the base of the humidification chamber to heat water within the chamber. Optionally, the heating element may be located within an opening or recess formed in a bottom portion of the upper housing 130.

A lid 120 covers the upper housing 130 to substantially enclose the humidification chamber within the housing 130. In one form, the lid 120 may be formed of plastic and may be at least about 4 mm thick throughout a significant portion of the lid 120 and preferably through substantially the whole of the lid 120. In this configuration, the thickness of the lid 120 provides the lid 120 with additional strength whilst allowing the upper exterior surface 121 of the lid 120 to maintain a substantially smooth and aesthetically appealing appearance. Reinforcing ribs 124 may be placed on the lower inner surface 122 of the lid 120 to further help reinforce and strengthen the lid 120. In some forms, the ribs 124 tend to distort the upper surface 121 of the lid and the result can be unattractive. A lid having a thickness of about 4 mm may reduce any distortion to the upper surface from the reinforcing ribs 124.

The lid 120 may be configured to be removable from the body 110 or the lid 120 may be hinged or otherwise connected to the body 110 of the apparatus 100 to allow access to the interior of the upper housing 130.

In one form, the lid 120 is connected to the body 110 with hinge assemblies 125. In the illustrated configuration, the lid 120 is connected to the rear of the body 110 using two hinge assemblies. The lid 120 can be connected to other surfaces. In addition, the lid 120 can be connected to the body 110 using as few as one hinge assembly 125 or more than two hinge assemblies 125. Preferably, the hinge assemblies 125 are constructed such that, with the lid 120 in the closed position (e.g., as shown in FIG. 1), the hinge assemblies 125 are generally flush with or recessed into the surface of the rear outer wall 132b. In some configurations, the hinge assemblies 125 are constructed such that the hinge assemblies do not protrude rearward of the rear outer wall surface 132b. In some configurations, some of the hinge features may protrude very slightly from one or more surrounding surface of the rear outer wall surface or other surrounding portion of the apparatus. In some configurations, the lid 120 comprises an outer perimeter and the hinge assemblies 125 do not protrude significantly outward of the outer perimeter of the lid 120.

Figure 3:
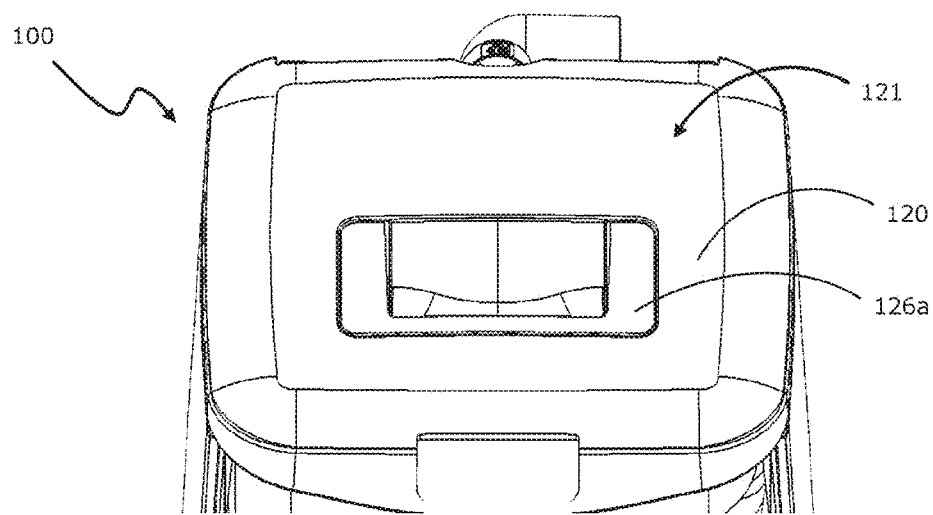
FIG. 3 is a top perspective view of an upper portion of one form of breathing assistance apparatus according to the invention and showing one form of lid that may be used with the apparatus.

As shown in FIG. 3, the lid 120 may comprise a handle 126 for easy maneuverability. Preferably, the handle 126 is located substantially centrally on the lid 120, but in other forms the handle 126 may be located further toward the front or rear of the lid 120 or even to one side of the lid 120. In one form, the handle 126 is hinged from the lid and is configured to move between a down position (such as a storage position) and a raised position in which the handle projects from the lid and is able to be held by a user in order to carry the apparatus. The handle may comprise a first surface 126a and a substantially opposing second surface. When the handle is in the down position, the first surface 126a may form an upper surface 126a that is substantially flush with or that is below the upper surface 121 of the lid 120. Therefore, when the handle 126 is in the down position, the apparatus 100 may be substantially devoid of protrusions extending from its upper surface 121.

By providing a breathing assistance apparatus 100 having a substantially flush upper surface 121 or an upper surface 121 that is at least substantially devoid of protrusions, the apparatus 100 may be kept substantially compact in order to take up minimal space during transportation and to reduce the risk of damage to otherwise protruding parts. The apparatus 100 may also be more aesthetically pleasing.

Figure 4:
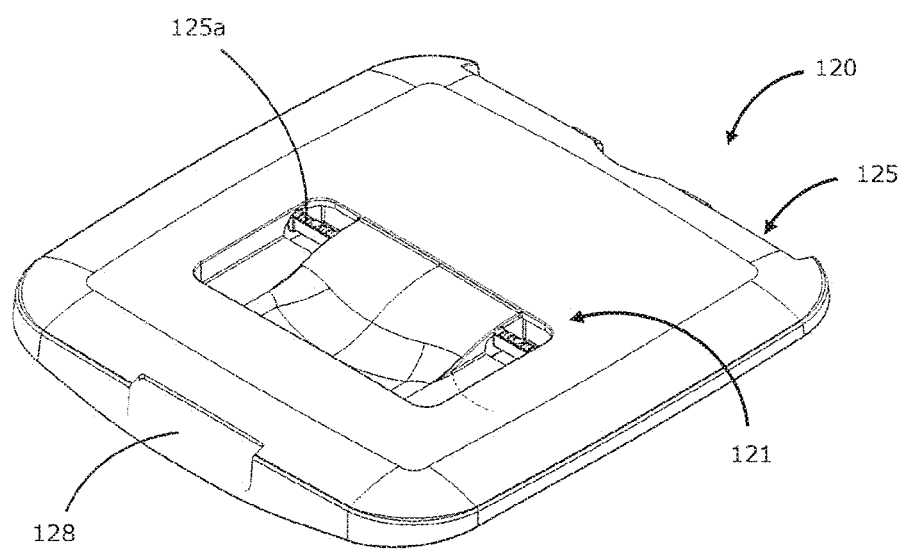
FIG. 4 is a perspective view of the lid shown in FIG. 3 and without the handle.
Figure 5:
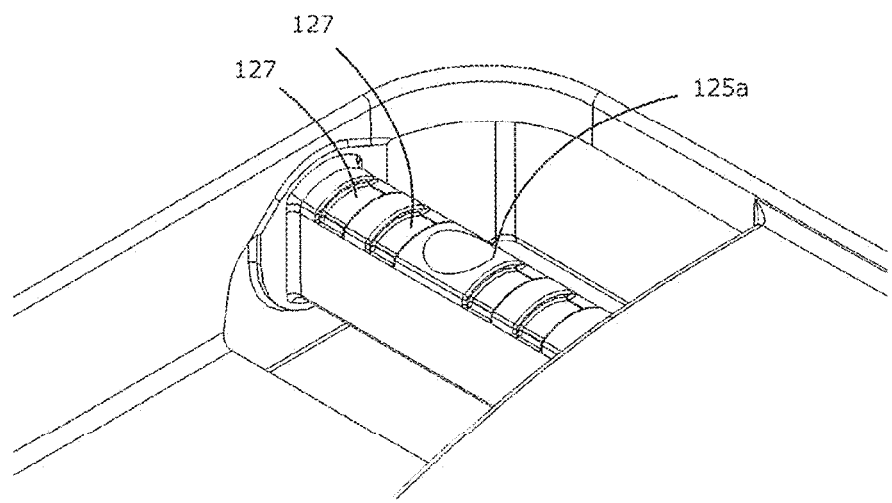
FIG. 5 is an enlarged view of a portion of the lid shown in FIG. 4 and illustrating grooved hinge members of the lid.

It has been found that hinged handles may sometimes squeak as the handle is moved between a down position and a raised position. To minimise squeaking of the handle 126 when it is moved, the handle 126 may be formed of a different material to the lid 120 or at least the hinge members of the handle 126 (that connect engage with hinged members of the lid 120 to form a hinge) may be formed of a different material to the connecting hinged members 125*a* of the lid 120. For example, the handle 126 or hinged members of the handle may be substantially formed of a polyester material and the lid or hinged members of the lid may be substantially formed of a polycarbonate material One or more grooves 127 may also be provided on the hinged members 125*a* of the lid to further minimize squeaking, as shown in FIGS. 4 and 5.

Figure 6:
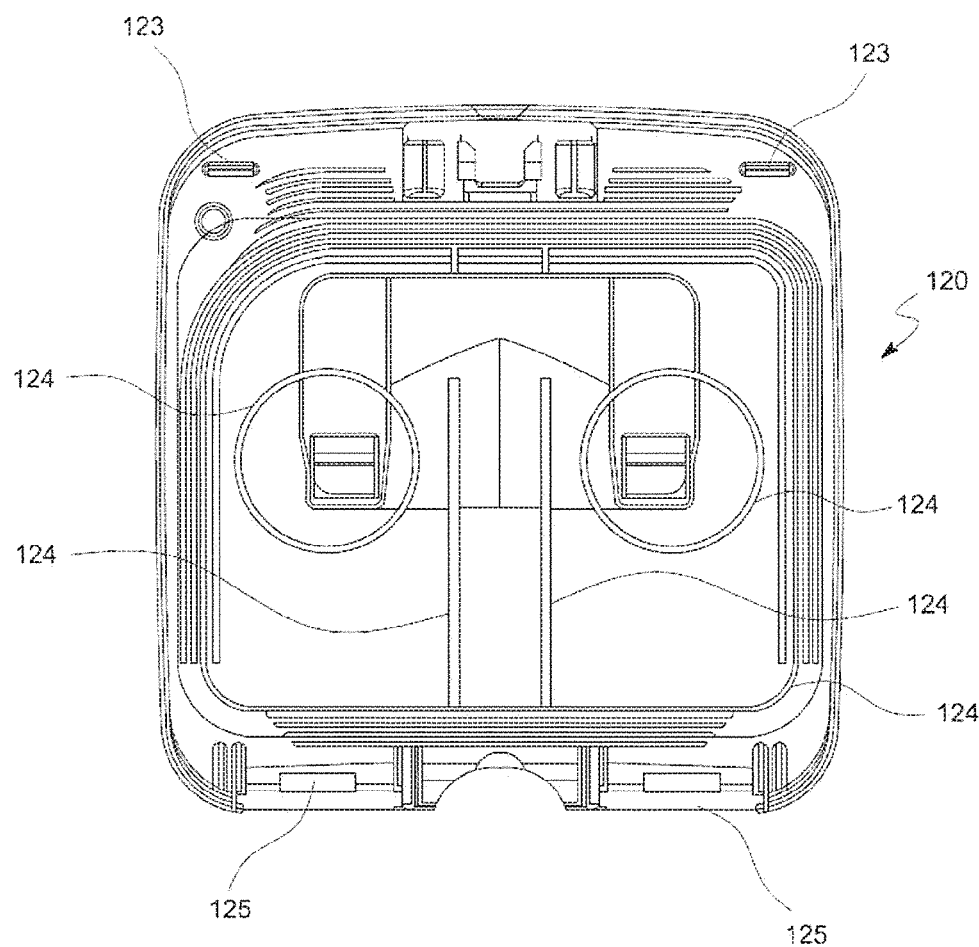
FIG. 6 is a bottom view of one form of lid that may be used with the apparatus of the invention, in which the lid comprises support members that project from the lower surface of the lid at each front corner.

Optionally, the lid 120 may also comprise one or more locks 128 to lock the lid 120 in the closed position. In one form, the lid 120 is hinged from the rear of the apparatus 100 and a lock, which comprises a latch 128, is provided at the front of the apparatus 100 to hold the lid 120 closed. Preferably, the latch 128 is provided at a central region at the front of an upper edge of the apparatus body 110. In this form, because only a central latch is provided (rather than a latch on either side of the lid), the lid may tend to rock from side to side. This may cause the apparatus 100, particularly the upper housing 130, to leak. To help prevent the lid 120 from rocking in this manner, one or more support members 123 may be provided between the lid and apparatus body. The support member(s) 123 may be configured to keep the lid substantially level with or substantially parallel to an upper surface of the apparatus body 110, such as an upper surface of the upper housing. In one form, the support member(s) 123 may be provided on the interior surface of the lid 120 at or near each front corner and/or the support member(s) 123 may be provided on an upper surface of the upper housing 130 at or near each front corner. In one form, the one or more support members 123 may be in the form of ridges or rails or the like that project from the interior surface at each front corner of the lid, as shown in FIG. 6. The support member(s) 123 may also help to prevent the lid from rocking side to side during use.

The illustrated body 110 of the apparatus comprises at least one outer surface 111. In the illustrated configuration, the body 110 comprises four generally planar outer surfaces 111 that are connected by rounded corners 112. Other configurations are possible.

Figure 7:
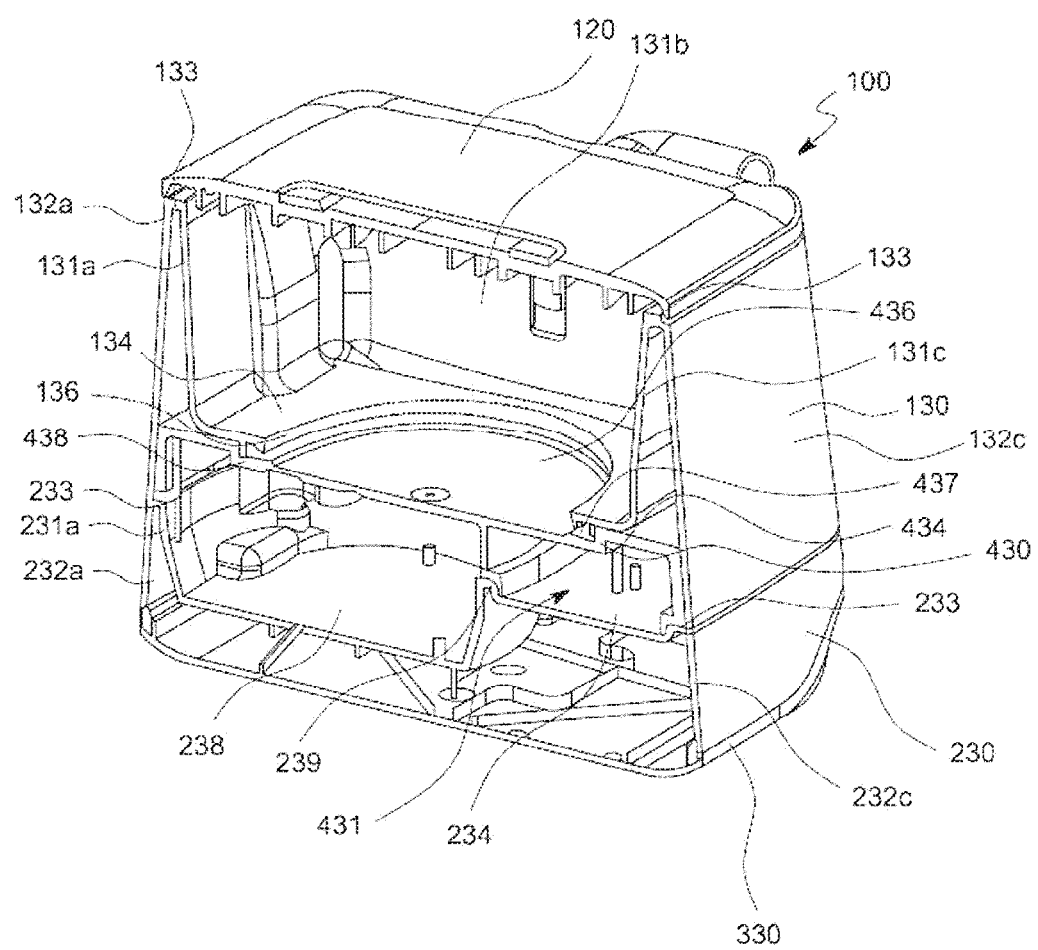
FIG. 7 is a cross-sectional perspective view of the embodiment shown in FIG. 1.

As shown in FIG. 7, the outer surface(s) of the body typically form(s) outer wall(s) of the upper and lower housings 130, 230 and base 330.

The upper housing 130 may comprise at least one inner wall 131 that defines an inner surface of the upper housing and at least one outer wall 132 that defines an outer surface of the upper housing. For example, the upper housing may comprise a substantially circular inner wall that is substantially adjacent to a substantially circular outer wall. In another form, the upper housing may comprise a plurality of inner walls and outer walls.

The inner wall 131 may comprise an inner surface that faces the interior of the upper housing 130 and an outer surface that faces away from the interior. Similarly, the outer wall 132 may comprise an inner surface that faces toward the interior of the upper housing 130 and an outer surface that faces away from the interior.

The inner 131 and outer wall(s) 132 may be integrally formed as a single part to avoid seams or joins between the walls 131, 132. In one form, the inner wall(s) 131 may be located substantially adjacent to and spaced apart from the outer wall(s) 132 so that the outer surface of the inner wall 131 substantially faces the inner surface of the outer wall 132. As shown in FIG. 7, an upper surface 133 may be provided at or near an upper edge of the inner 131 and outer 132 walls and may span the distance between upper edges of the inner and outer walls 131, 132. In one form, the inner and outer walls 131, 132 are configured so that the inner wall(s) 131 appear(s) to be substantially folded back on the outer wall(s) 132. In this form, the upper surface 133 that joins the inner and outer walls 131, 132 also forms a 'folded' region. By providing an upper housing 130 having inner and outer walls 131, 132 without a seam or join between the walls 131, 132, it is possible to reduce the risk that water or other liquids may seep between the join and enter into the lower housing 230 below.

Figure 8:
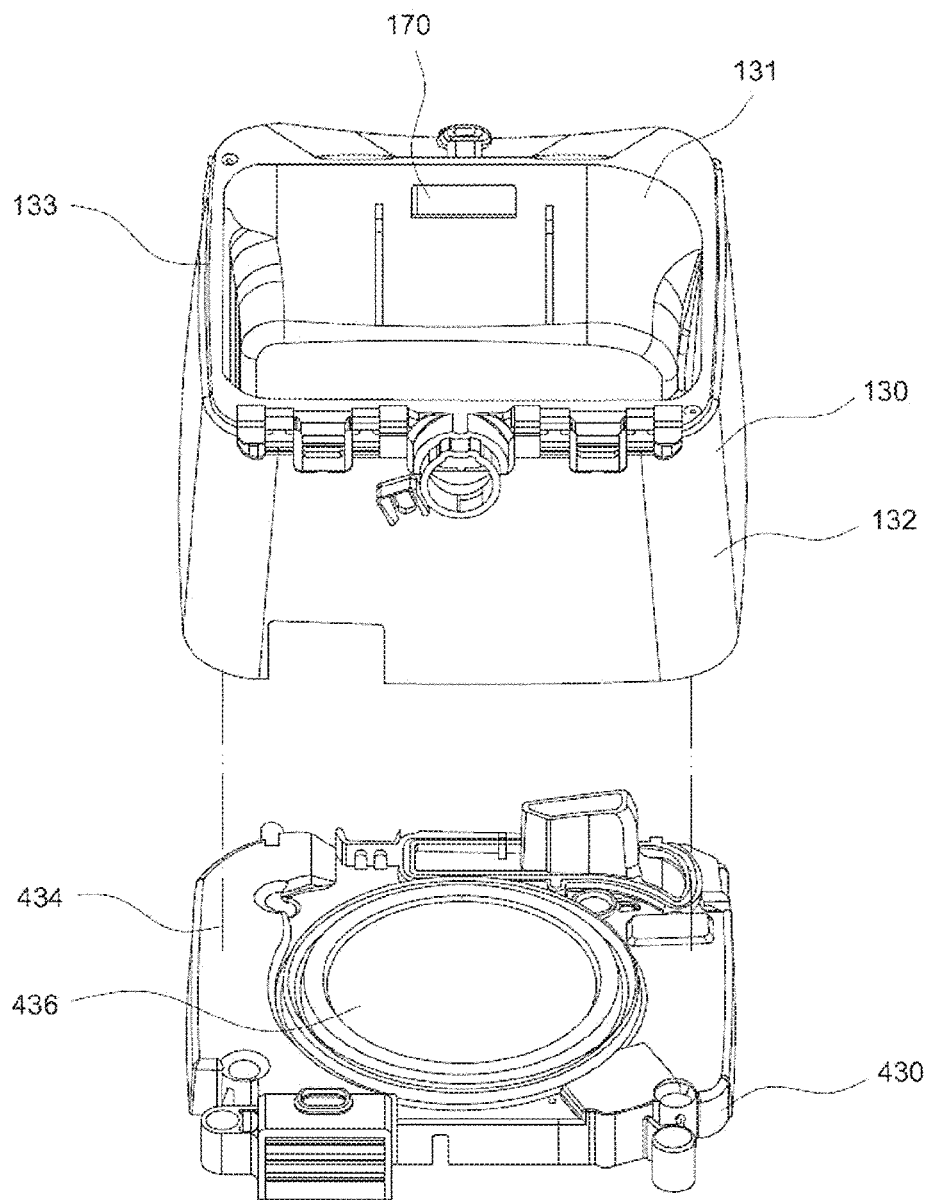
FIG. 8 is an exploded view showing one form of upper housing and sub-housing that may be used with the apparatus of the invention.
Figure 9:
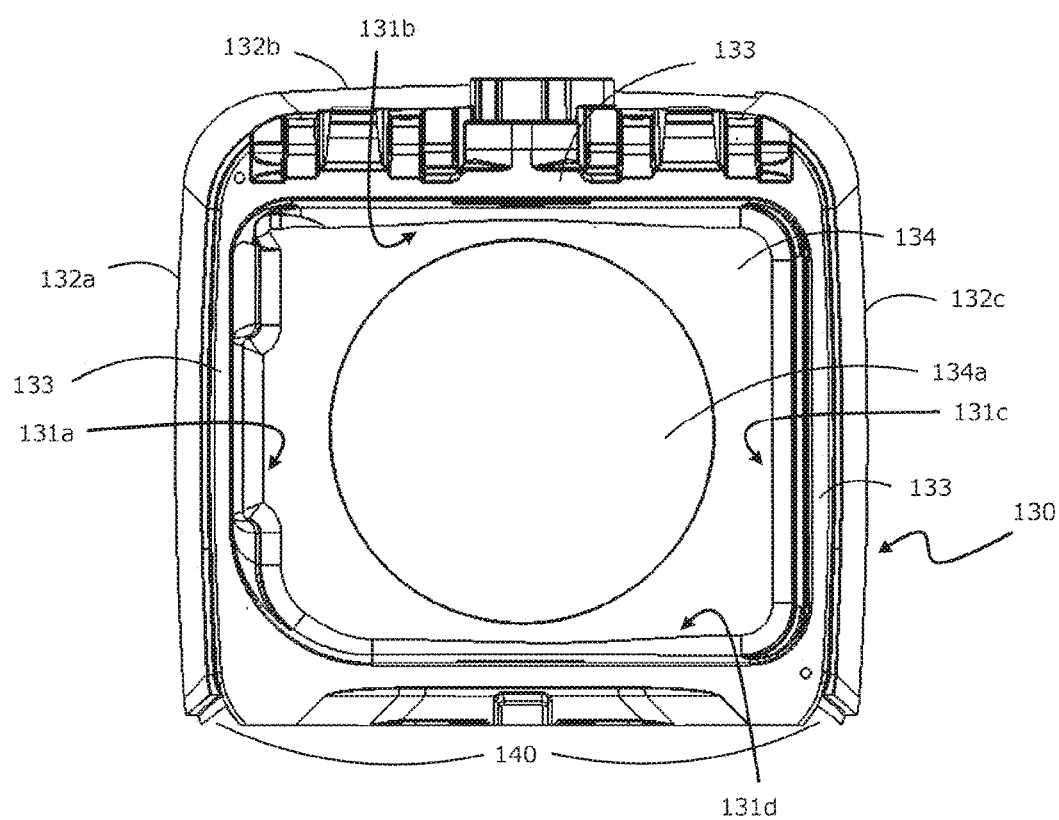
FIG. 9 is a top view of one form of upper housing that may form part of the apparatus of the invention.

In one form, the upper housing 130 may comprise at least three inner walls forming substantially opposing inner side walls 131*a*, 131*c*, an inner rear wall 131*b* extending between the inner side walls and an inner front wall 131*d* that substantially opposes the inner rear wall 131*b*. A lower wall 134 may be connected to and located between the inner walls 131*a*, 131*b*, 131*c*, and 131*d* to form the floor of the upper housing. In this configuration, the upper housing 130 may form an enclosure for a humidification chamber Optionally, an opening or recess 134*a* may be provided in the lower wall 134 for locating a heating element therein, as shown in FIGS. 7 to 9. Preferably, the heating element is supported by a sub-housing 430 that is located beneath the opening 134*a*. The sub-housing 430 may be an internal structure that is configured to be located between the upper and lower housings 130, 230. In one form, the sub-housing 430 may be configured to comprise a floor that substantially extends across and below the opening 134*a*, as shown in FIG. 7, to support the heating element and humidification chamber thereon.

In one form, the floor of the sub-housing 430 comprises a recessed region 436 configured to be located beneath the opening 134*a* of the upper housing 130 when the apparatus 100 is assembled. Preferably, the recessed region 436 is wider than the opening 134*a* so that a channel 437 is formed between a lower surface of the recessed region 436 and a bottom surface of the upper housing floor 134. The periphery of the recessed region 436 may form an outer wall 438 of the channel 437. Optionally, a peripheral wall 136 substantially surrounds the opening 134*a* and projects downwardly from the bottom surface of the upper housing floor 134 and a gap is formed between the distal end of the peripheral wall 136 and the recessed region 436. The channel 437 formed between the peripheral wall 136, outer wall 438, and recess region 436 may be configured to hold an outer edge of a heating element therein to help hold the heating element in position. A humidification chamber (not shown) may be located above the heating element and may be substantially held in position by inner walls that define the opening 134*a* in the floor of the upper housing 130.

The shape of the exterior of the upper housing 130 may be similar to that of its interior. For example, the exterior of the upper housing 130 may comprise three outer walls forming substantially opposing outer side walls 132*a*, 132*c* and an outer rear wall 132*b* extending between the outer side walls 132*a*, 132*c*. The outer side walls 132*a*, 132*c*, and rear wall 132*b* may be located substantially adjacent to and spaced apart from the inner side walls 131*a*, 131*c* and rear wall 131*b* respectively to form three pairs of inner and outer walls. In this configuration, a gap 140 is provided at the front of the upper housing 130 between the outer side walls 132*a*, 132*c*.

A face plate 141 may be located within the gap 140 between the outer side walls 132*a*, 132*c*. For example, a face plate may be located substantially adjacent to the unpaired inner front wall 131d. In one form, the face plate 141 may substantially extend from one front corner of the upper housing 130 to the other front corner. The face plate 141 may comprise a user interface through which a user may control the apparatus 100.

Although in a preferred form, the upper housing 130 comprises four inner walls 131 and three outer walls 132, as described above, it is envisaged that other configurations are possible.

Figure 10:
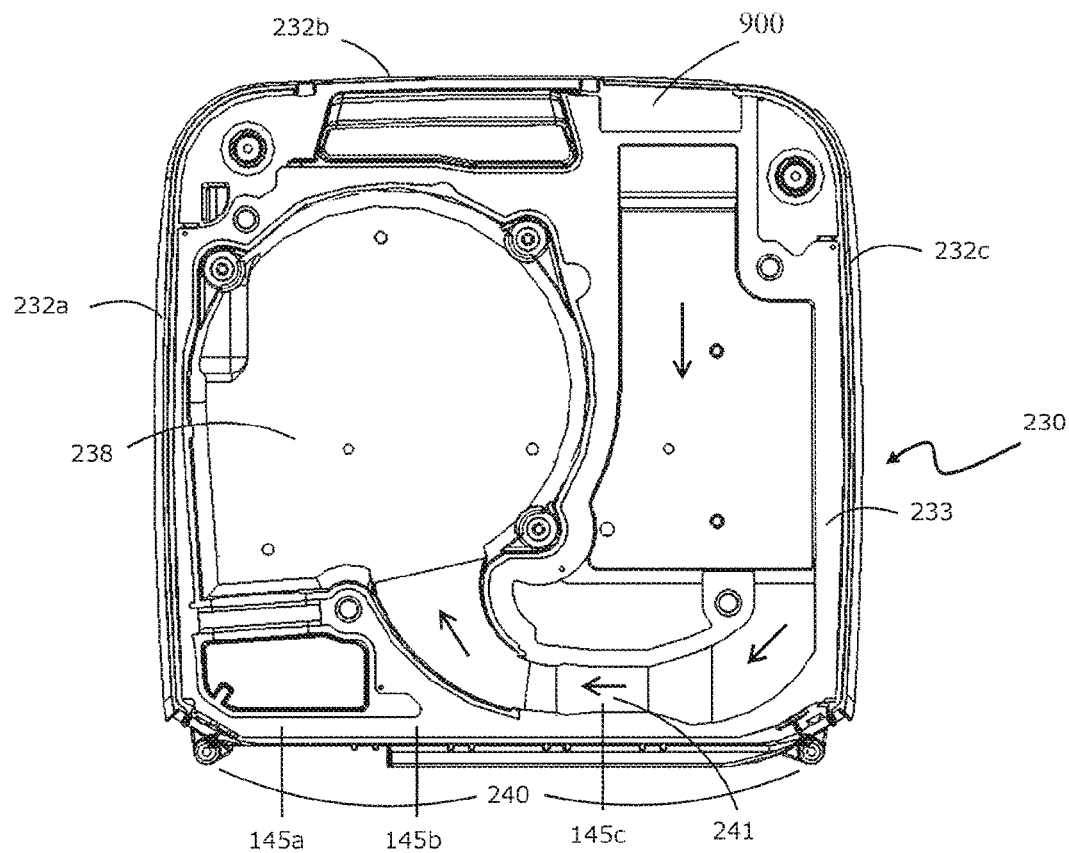
FIG. 10 is a top view of one form of lower housing that may form part of the apparatus of the invention indicating the air flow from an air inlet to the blower and possible locations of sensors.

Turning now to FIGS. 7 and 10, the lower housing 230 may comprise at least one inner wall 231 that defines an inner surface of the lower housing and at least one outer wall 232 that defines an outer surface of the lower housing. The inner wall 231 may comprise an inner surface that faces the interior of the lower housing 230 and an outer surface that faces away from the interior. Similarly, the outer wall 232 may comprise an inner surface that faces toward the interior of the lower housing 230 and an outer surface that faces away from the interior.

As described above and shown in FIG. 7, to help prevent water or other forms of liquid entering a join between the inner and outer wall(s) of the lower housing 230 and into the base below, the adjacent inner 231 and outer 232 wall(s) of the lower housing 230 may be integrally formed as a single part. For example, the inner wall(s) 231 may be located substantially adjacent to and spaced apart from the outer wall(s) 232 so that the outer surface of the inner wall 231 substantially faces the inner surface of the outer wall 232. An upper surface 233 may be provided at or near an upper edge of the inner 231 and outer 232 walls. The upper surface 233 may span the distance between upper edges of the inner and outer walls 231, 232. In one form, the inner and outer walls 231, 232 are configured so that the inner wall(s) 231 appear(s) to be folded back on the outer wall(s) 232. In this form, the upper surface 233 that joins the inner and outer walls 231, 232 also forms a 'folded' region.

As shown in FIGS. 7 and 10, the lower housing 230 may comprise inner 231 and outer 232 walls of the same or a similar configuration to the inner 131 and outer 132 walls of the upper housing 130, as described above. Other configurations are also possible. For example, the lower housing may comprise a substantially circular inner wall that is substantially adjacent to a substantially circular outer wall.

In one form, the lower housing may also comprise four inner walls 231 comprising substantially opposing side walls 231a, 231c, a rear wall 231b extending between the side walls 231a, 231c and a front wall 231d substantially opposite the rear wall.

A lower wall 234 may be connected to and located between the inner walls 231 to form a floor of the lower housing 230. In one form, as shown in FIG. 7, outer walls 232 of the lower housing may extend below the floor of the housing. For example, the floor 234 may be located substantially near the top edge of the inner 231 and outer walls 232. In one form, the distance between the top edge of the inner wall 231 and the floor 234 may be so small that the inner wall and upper surface 233 of the wall structure form a lip that substantially defines the periphery of the floor 234. In one form, a recess 238 may be formed in the floor 234 of the lower housing for locating a blower therein. A raised lip 239 may also be formed in the floor 234 to define the periphery of the recess 238. The blower (not shown) may be configured to blow breathing gas into the humidification chamber in order to humidify the gas.

In one form, the sub-housing 430 comprises a guide configured to rest on or engage with the raised lip 239 of the lower housing. Additionally, or alternatively, the sub-housing 430 may comprise an outer guide configured to engage with or rest on the upper surface 233 of the lower housing wall configuration in order to help located the sub-housing on the lower housing 230.

The shape of the exterior of the lower housing 230 may be similar to that of its interior. For example, the exterior of the lower housing 230 may comprise three outer walls forming substantially opposing outer side walls 232a, 232c and an outer rear wall 232b extending between the outer side walls 232a, 232c. The outer side walls 232a, 232c, and rear wall 232b may be located substantially adjacent to and spaced apart from the inner side walls 231a, 231c and rear wall 231b respectively to form three pairs of inner and outer walls. In this configuration, a gap 240 is provided at the front of the upper housing 230 between the outer side walls 232a, 232c. A face plate 141 may be located within the gap to form a front surface of both the upper and lower housing. The face plate 141 may therefore form an outer wall for both the upper 130 and lower 230 housing or for just the upper housing 130 or just the lower housing 230.

A seal may be located between an upper edge of the face plate 141 and the upper 130 or lower housing 230, as the case may be, to help prevent water seeping between the face plate and housing. Preferably, the face plate 141 forms an outer wall for both the upper and lower housing 130, 230 and a seal is located on the top edge of the face plate 141 and abuts an upper edge of the upper housing 130.

Figure 11:
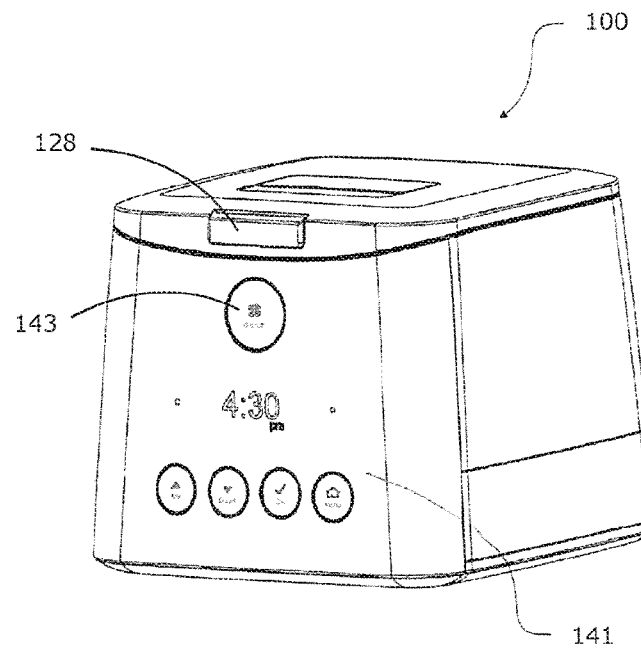
FIG. 11 is a perspective view of one form of breathing assistance apparatus according to the invention in which the face plate at the front of the apparatus provides a user interface.

In one form, the face plate 141 may be tinted in whole or in part. For example, only an outer border of the face plate 141 may be tinted. Alternatively, substantially the whole of the face plate 141 may be tinted. The face plate 141 may be configured to provide a user interface comprising one or more images and/or user inputs to monitor and/or control the operation of the breathing assistance apparatus 100, as shown in FIG. 11. In some forms, the face plate 141 may comprise a plastic or glass screen with a backlit display. For example, an LED screen may be located behind and visible through the tinted 141 face plate. In this form, the face plate 141 also acts as a screen for the user interface.

Where substantially the whole of the face plate 141 is tinted, it may appear that the screen is larger and more integral with the body 110 of the apparatus. This configuration may be aesthetically appealing. In this configuration, less aesthetically pleasing components, such as electronic components for example, that are located behind the face plate 141 may also be less visible or may not be visible at all. Furthermore, the face plate 141 may be configured to align tidily with the substantially opposing outer side walls of the apparatus 100 to form a substantially flush or aesthetically appealing join, as shown in FIG. 11.

Preferably, the apparatus 100 comprises an electronic user interface in whole or in part. In this form, a PCB may be located behind the face plate 141 to control the user inputs and/or to control illuminated images that may be visible through the face plate 141 during use. One or more user inputs 142 may comprise mechanical buttons, switches, dials, or the like that are electrically connected to the PCB and that project in part through apertures formed in the face plate for access by a user. Additionally or alternatively, one or more user inputs 142 may comprise electronic buttons or dials that may be operated using any suitable system, such as by capacitive sensing in which the buttons or dials may be activated by the user lightly touching the face plate, for example.

A substantially compressible facing may be located behind the face plate 141 so as to be sandwiched between the face plate 141 and the PCB. The facing may help provide damping to the PCB by absorbing at least part of an impact shock to the apparatus, particularly an impact to the face plate of the apparatus. In this way, the facing may help protect the electronic components of the PCB from damage if the face plate 141 were otherwise knocked against the PCB components. The facing may be formed of any suitably compressible material, such as rubber or silicone for example. The facing may comprise one or more apertures through which user inputs may project. Optionally, one or more apertures of the facing may align with one or more apertures of the face plate 141 so that user inputs may project from the PCB and through the aligned apertures for access by a user. In another form, the facing may comprise one or more apertures that align with an electronic component on the PCB that may be illuminated during use. For example, the facing may comprise an aperture that aligns with the screen of an LED lit electronic clock located on the PCB and visible through the face plate 141.

In one form, the substantially compressible facing may comprise arms that extend through apertures formed in the PCB to press against an outer surface of the adjacent inner wall of the housing, such as the upper housing 130, the lower housing 230, or both the upper and lower housings 130, 230. For example, the facing may comprise a first portion located between the PCB and the face plate, a second portion located between the PCB and interior structures of the apparatus, and one or more arms that project through apertures in the PCB and connect the first and second portions of the facing. In this arrangement, the PCB may be supported by and easily attached to the facing. The compressible facing, extending from both the front and rear surfaces of the PCB may also help to protect the PCB from impact forces from both the front and rear.

In one form, as shown in FIG. 11, a user input in the form of a power switch 143 is provided on the face plate 141 to power the apparatus 100 on or off. The power switch 143 may be located proximate to the locking latch 128 of the lid 120 to provide for one handed operation by a user. In this configuration, a user can close the lid 120 and move their thumb or finger downward to activate the power switch 143 to power the apparatus 100 on. This configuration may provide a quick and simple method for a user to operate the latch 128 and power switch with one hand. Similarly, the user can place their hand on the lid 120, turn off the power button 143 to turn the apparatus 100 off and then move their thumb or finger to the latch 128 to release the latch 128 and open the lid 120. Again, these steps may be carried out quickly and easily with one hand. These steps may be further simplified where the latch 128 may be released by a button and where the power switch 143 is in the form of a button that can be depressed to turn the apparatus 100 on or off. Preferably, the latch 128 is located substantially directly above the power switch 143 and within a distance in which a typical user's thumb may reach without substantially moving the user's hand. For example, the latch 128 may be located within about 10 cm of the power switch 143. It should be appreciated that, although it is preferred for the power switch to be in the form of a button, it is envisaged that the power switch could otherwise be in the form of a lever switch, dial, or other suitable user input without departing from the invention.

Figure 12:
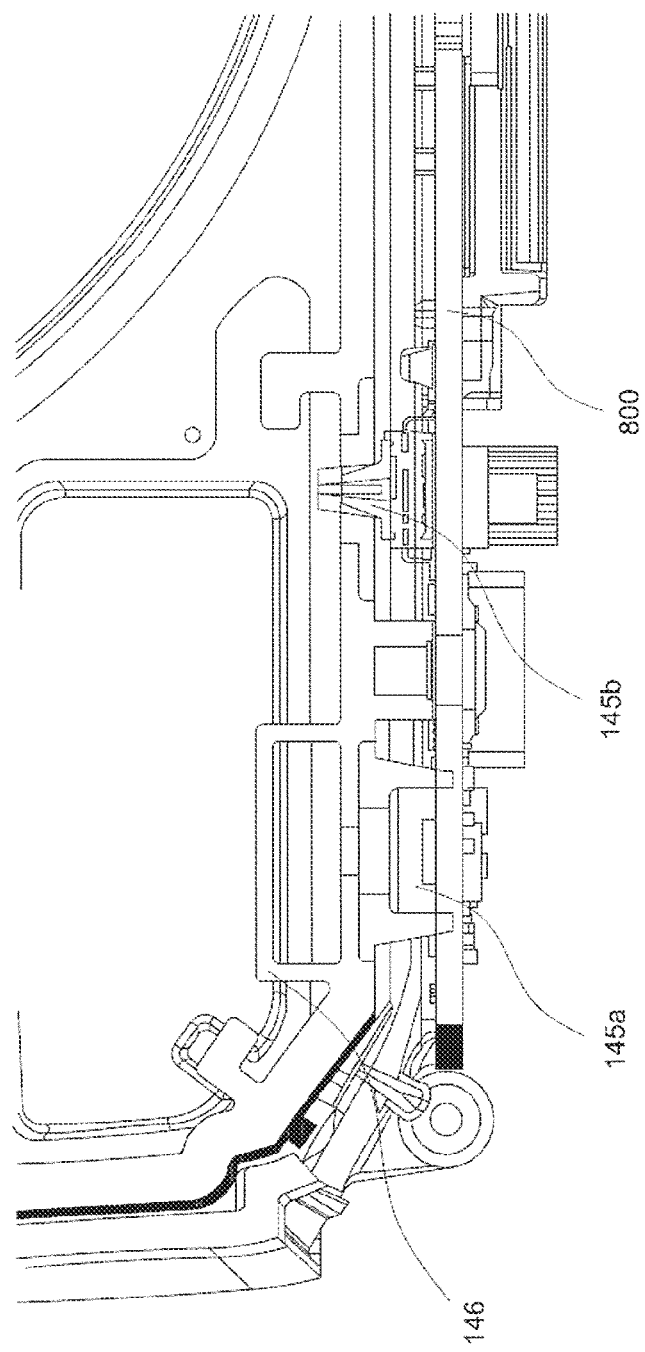
FIG. 12 is a cross-sectional top view of a portion of one form of sub-housing and lower housing and showing some of the electronic components, including sensors, located near the front wall of the apparatus.

In one form, as shown in FIGS. 10 and 12, the apparatus 100 may be configured so that one or more of the sensors 145 are located for easy accessibility in order to service or replace the sensors when required. For example, a humidity sensor 145a may be located near the outer wall structure of the apparatus and in an air flow path between the blower and the humidification chamber Preferably, the humidity sensor 145a is located on the sub-housing substantially above the area indicated in FIG. 10. By positioning the humidity sensor downstream of the blower and upstream of the humidification chamber, the readings of the humidity sensor 145a may be more accurate compared to when the sensor 145a is placed upstream of the blower. This is because exhaled air from the patient may return along the breathing gas flow path toward the blower and may cause the humidity of the breathing gas upstream of the humidification chamber to increase above humidity levels upstream of the blower.

Optionally, the apparatus comprises a baffle located within the air flow path between the humidity sensor 145a and the blower. The baffle may be configured so that air exiting the outlet of the blower may contact the humidity sensor 145a but is not aimed directly at the humidity sensor 145a. Preferably, the baffle 146 is located within the sub-housing. In one form, the baffle 146 comprises a substantially u-shaped wall that projects from an interior wall of the sub-housing 430 and into the air flow path. The humidity sensor may also project from the interior wall of the sub-housing 430 and may be located between the arms of the U. A gap may be provided between the floor of the air flow path and a lower edge of the baffle wall 146 so that air may pass through the gap and behind the baffle 146 where the humidity of the air may then be measured by the humidity sensor 145a. In another form, a gap may be provided between the ceiling of the air flow path and an upper edge of the baffle wall 146. In yet another form, a first gap may be provided beneath the lower edge of the baffle wall and a second gap may be provided above the upper edge of the baffle wall. In these arrangements, air from the flow path is in contact with the humidity sensor 145a but is not blown directly at the sensor 145a, so that more accurate sensor readings may be obtained. In one form, the apparatus comprises a humidity sensor 145a, to measure the humidity of air, and a flow sensor 145c to measure air flow to provide an indication of how much power is provided to the heating plate. The flow sensor may be located in a venturi 241 through which air flows from an air inlet 900 to the blower. One suitable location for the flow sensor 145c is indicated in FIG. 10.

Air exiting the blower may flow along a flowpath to the upper housing 130 and through a flowpath in the upper housing to an air inlet of the humidification chamber.

In one form, pressure and humidity sensors may be located in the sub-housing 430 and immediately downstream of the blower.

In one form, a pressure sensor 145b may be located in the sub-housing at a distance from the blower to reduce the likelihood that air flowing from the outlet of the blower could adversely affect the pressure readings, particularly as a result of fluctuations in the blower motor. By locating the pressure sensor 145b away from the flowpath of outlet air from the blower, it may be possible to obtain more accurate pressure readings. In a preferred arrangement, the pressure sensor 145b is located on the sub-housing 430 substantially above the area indicated in FIG. 10 and as shown in FIG. 12.

In one form, two or more sensors 145 are located on one face of the PCB 800 and are configured to project from an interior surface of a first wall of the sub-housing and into the air flow path. For example, each sensor 145 may be mounted on an inner face of the PCB. Each sensor 145 may project from the PCB 800 and through a respective aperture of the sub-housing 430 so as to project into the air flow path. Alternatively, the sensors 145 are configured to project through apertures located on a first wall of the upper housing 130 or of the lower housing 230 so as to project into the air flow path.

In one form, the first wall comprises the front wall of the sub-housing and the PCB 800 is located between the face plate 141 and front wall of the sub-housing 430. In another form, the first wall comprises the front wall of the inner and/or outer walls 131, 132 of the upper housing 130 and the PCB 800 is located between the face plate 141 and the first wall. In a further form, the first wall comprises the front wall of the inner and/or outer walls 231, 232 of the lower housing 230 and the PCB 800 is located between the face plate 141 and the first wall.

By placing two or more sensors 145 on an interior face of the PCB 800 so that the sensors 145 are aligned with apertures formed on a first wall of the sub-housing 430, upper housing 130, or lower housing 230, it is possible to easily install the sensors 145 in one movement by pushing the PCB 800 against the exterior surface of the first wall so that the sensors 145 are pushed through the respective apertures in the sub-housing 430, upper housing 130, or lower housing 230, to project from the interior surface of the first wall. In one form, soft seals are provided over the apertures in the sub-housing 430. Each soft seal is configured to receive a sensor therein. Preferably, the soft seals are co-moulded to the sub-housing 430, upper housing 130, or lower housing 230. In this arrangement, during assembly the sensors 145 may be pushed through the apertures in the sub-housing 430, upper housing 130, or lower housing 230, and into the soft seals 147, as shown in FIG. 12. Co-moulding the soft seals onto the housing 430, 130, 230 simplifies assembly of the breathing assistance apparatus 100, as the step of placing seals individually onto the sensors or into the apertures is removed, and fewer individual parts are required during assembly.

The sensors 145 may be connected to a control system comprising a control unit, which is typically located on the PCB 800. In one form the control unit may be a processor or microprocessor. The control unit is able to receive signals from the sensors and convert these signals into measurement data, such as air pressure data, air humidity data, and power output from the heating plate, for example. In some forms, the control system may be configured to control and vary the operation of various components of the apparatus to help ensure that particular parameters (such as air pressure, humidity, and power output for example) fall within desired ranges or meet desired thresholds or values. Typically, the desired ranges, thresholds or values are predetermined and are programmed into the control unit of the control system.

Preferably, one or more sensors 145 and the PCB 800 are located near the face plate 141, such as behind the face plate, so that removal of the face plate 141 allows the sensors 145 to be easily accessed for servicing or replacement, if required.

Although the face plate 141 has been described as forming an outer surface/outer wall for both the upper 130 and lower 230 housing, in other configurations, the face plate 141 may form the outer surface/outer wall of just the upper housing 130 or just the lower housing 230. In such a configuration, the housing that does not employ the face plate 141 as an outer surface/outer wall may instead comprise an outer wall substantially adjacent to each inner wall of that housing. In one form, the apparatus 100 may be configured so that the face plate 141 forms at least part of an outer surface/outer wall for the upper housing 130, the lower housing 230, and the base 330.

Even though the construction of the apparatus 100 is such that liquid is less likely to enter the underside of the upper 130 and lower 230 housings, the lower housing 230 may comprise one or more drainage channels. The drainage channels are configured to allow any water or other liquid within the housing 230 to drain away from the underside of the upper housing 130 to avoid the risk that the liquid could otherwise come into contact with the electronic components within the lower housing 230. The lower housing 230 may comprise one or more outlets through which liquid from the drainage channel(s) may exit the apparatus 100. In one form, one or more outlets may be located in the rear wall of the apparatus 100. In another form, one or more outlets may be located on a side wall of the apparatus 100. In one form, one or more outlets may be located near one or both front corners of the apparatus 100. For example, one or more drainage channels may be located along one or both sides of the apparatus 100 and may terminate in outlets provided at the front, side or rear of the apparatus. Preferably, a drainage channel is provided along each side of the lower housing 230 and each channel terminates in an outlet provided at the respective side of the apparatus 100 and near a front or rear corner of the apparatus 100. Preferably, the outlet(s) is/are located at or near the join between the upper 130 and lower housing 230.

The base 330 may comprise an exterior surface that is shaped to be similar to that of the lower housing 230. In one form, the exterior surface of at least an upper portion of the base 330 is substantially the same shape and dimensions as a lower portion of the lower housing 230 so that when the base 330 and lower housing 230 are connected together, a substantially flush outer surface is provided across the two parts 230, 330. Preferably, the base comprises substantially opposing side walls 331a, 331c, and a rear wall 331b extending between the two side walls. A lower wall may be located may be connected to and located between the side walls and rear wall to form the floor of the base 330, on which a PCB 400 and various electronic components may be supported. The wall(s) 331 of the base may be substantially short so as to form a lip surrounding at least a portion of the periphery of the base 330. In one form, the base 330 also comprises a front wall that is located substantially opposite the rear wall and that extends between the side walls. In another form, a gap is provided at the front of the base and between the two side walls. The gap may be configured to receive at least a portion of a face plate 141 therein.

Figure 13:
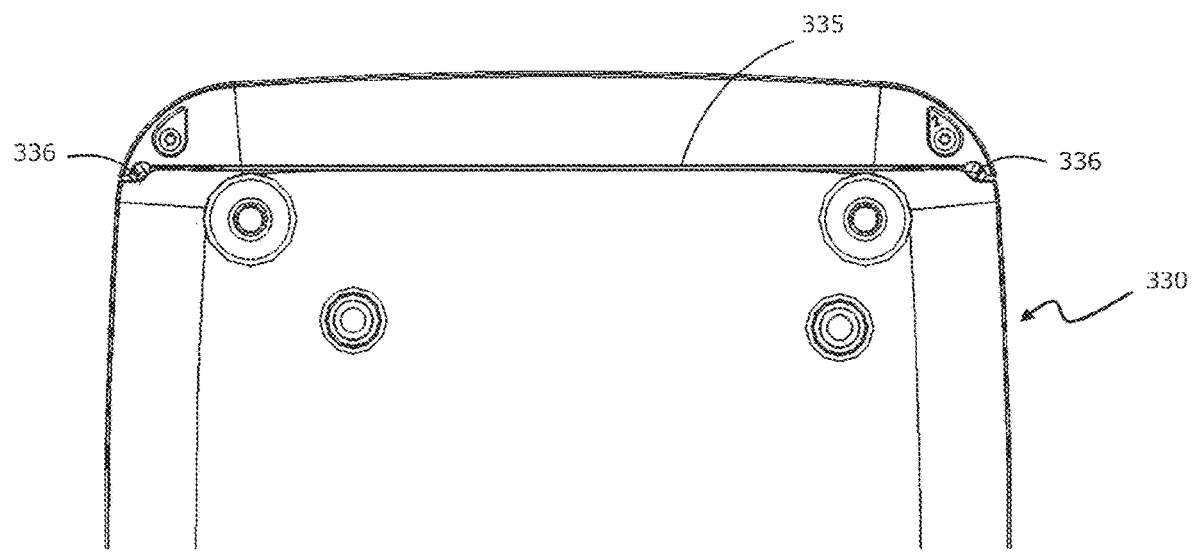
FIG. 13 is a bottom view of a portion of the base in which a drainage channel is shown.
Figure 14:
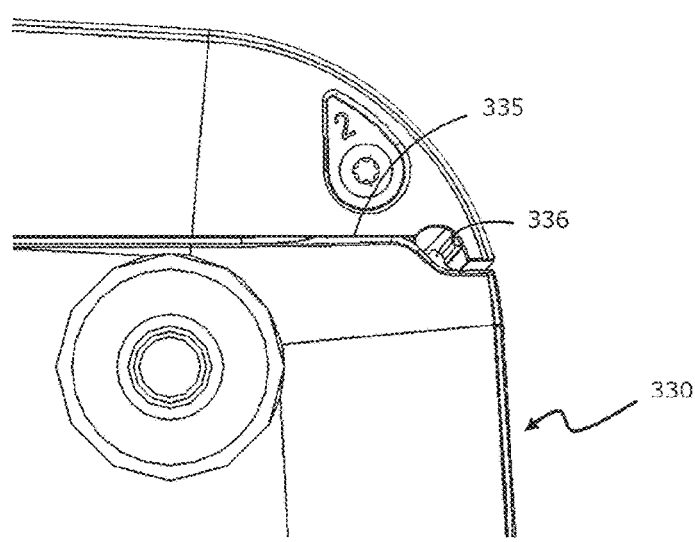
FIG. 14 is an enlarged view of a drainage channel shown in FIG. 12.

In one form, the control system may comprise a printed circuit board (PCB) 400, for controlling various operations of the apparatus. The PCB 400 may be located between the underside of the lower housing 230 and the base 330. Because the base 330 may be configured to house a PCB 400 and other electronic components, it is important that the electronics are kept as dry as possible. Therefore, the base 330 may comprise one or more drainage channels 335 to drain away liquid from the base 330 and to help prevent liquid from coming into contact with the sensitive electronic components, As shown in FIGS. 12 and 13, the drainage channel(s) 335 in the base 330 may connect with one or more outlets 336, which may be located at the side of the apparatus 100, the rear of the apparatus 100, and/or the front of the apparatus. In one form, one or more drainage channels may be located along one or both sides of the apparatus 100 and may terminate in outlets 236 provided at the front, side, or rear of the apparatus. Preferably, a drainage channel is provided along each side of the base 330 and each channel terminates at an outlet provided at the respective side of the apparatus 100 and near a front or rear corner of the apparatus 100. In one form, one or more drainage channels may each terminate at an outlet located near the front edge of the base 330, such as between the base 330 and the face plate 141 for example.

Figure 15:
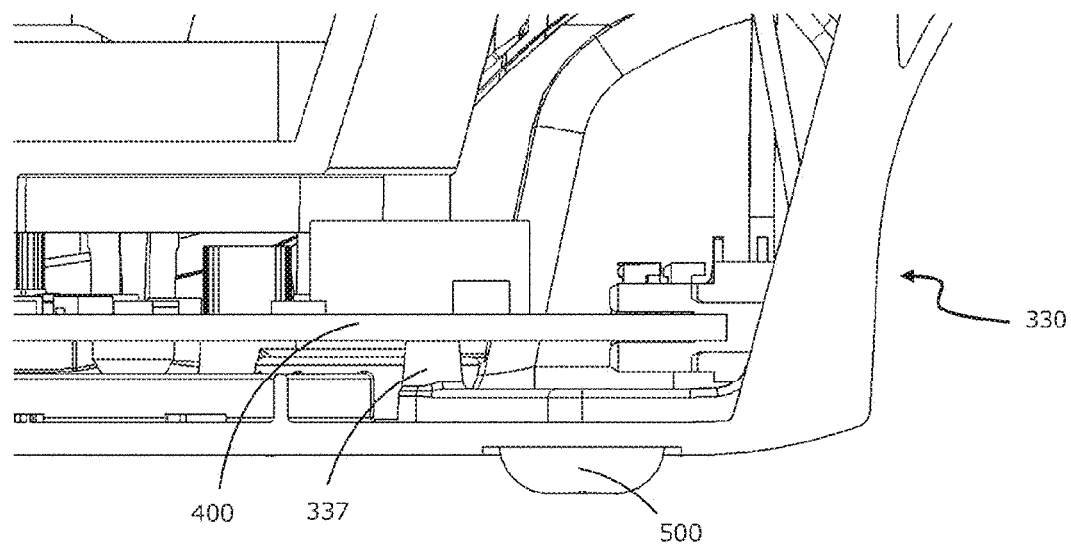
FIG. 15 is a cross-sectional view of a portion of one form of base for use with the apparatus of the invention.

Preferably, the PCB 400 rests on one or more compressible supports 337 within the base, as shown in FIG. 15. The compressible supports may be of any suitable construction, such as rubber or silicone columns for example. The compressible support(s) 337 may help to protect the PCB 400 and its electronic components and connections from breaking under at least some impact forces.

Figure 16:
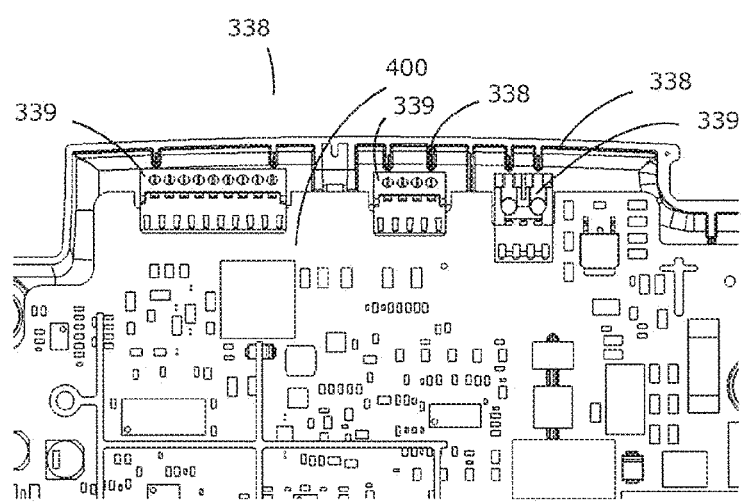
FIG. 16 is a top view of a portion of one form of base for use with the apparatus of the invention.

To help prevent dislodgement of electronic connectors to the PCB 400, the base 330 may comprise one or more guides 338 to hold the electrical connectors 339 in a desired position, as shown in FIG. 16. In one form, the guide(s) 338 may comprise one or more arms located along an inside wall of the base 330. The one or more guides 338 may be arranged to project toward one or more electrical connectors 339 and to press against the connectors 339 to ensure that the connectors 339 do not move from the desired position when the apparatus 100 is knocked or subjected to an impact force, for example.

In some forms, it may be preferable to include a safety mechanism within the breathing assistance apparatus to help ensure that the heating element of the apparatus does not overheat and fail or catch fire. In prior art breathing assistance apparatuses, a mechanical cut-off switch was used to disable power to the heating element if the cut-off switch was tripped, such as if the measured temperature of the heating element exceeds a first predetermined threshold. In one form, the apparatus of the invention may use the same prior art system.

In another form, the electronic control system of the apparatus may form a safety mechanism that protects against overheating by the heating element. In this form, the control system may be programmed using software configured to control the operation of the heating element. For example, the heating element may be configured to operate below a desired maximum operating temperature threshold. In one form, the desired maximum temperature threshold may be a temperature between approximately 60° C. and 70° C., such as 65° C. If the temperature of the heating element exceeds a predetermined temperature threshold, such as the maximum operating temperature or a temperature slightly higher than the desired maximum operating temperature, the control system may disable power to the heating element. In other words, the programmable control system may control the heating element temperature by modulating power to the heating element, such as by maintaining an electrical connection to provide power to the heating element and by disabling the electrical connection to disable power to the heating element. The control system may be configured to cause power modulation by using the control unit to control the operation of one or more components of the control system by sending electronic signals to one or more components of the system. One or more components of an electronic protection circuit (described in further detail below) may also be configured to provide feedback to the control unit via electronic signals. In this way, the control system may be configured to cause the heating element to substantially maintain (or at least not exceed) a predetermined temperature.

An electronic signal used in the control system may be any suitable form of signal, including the introduction of a signal where no signal was already present, a change to an existing signal, or a discontinuation (temporary or permanent) of an existing signal between the control unit and one or more components of the control system.

The apparatus may be configured in different ways to control the heating element temperature and to provide protection systems to prevent overheating of the heating element.

Figure 17:
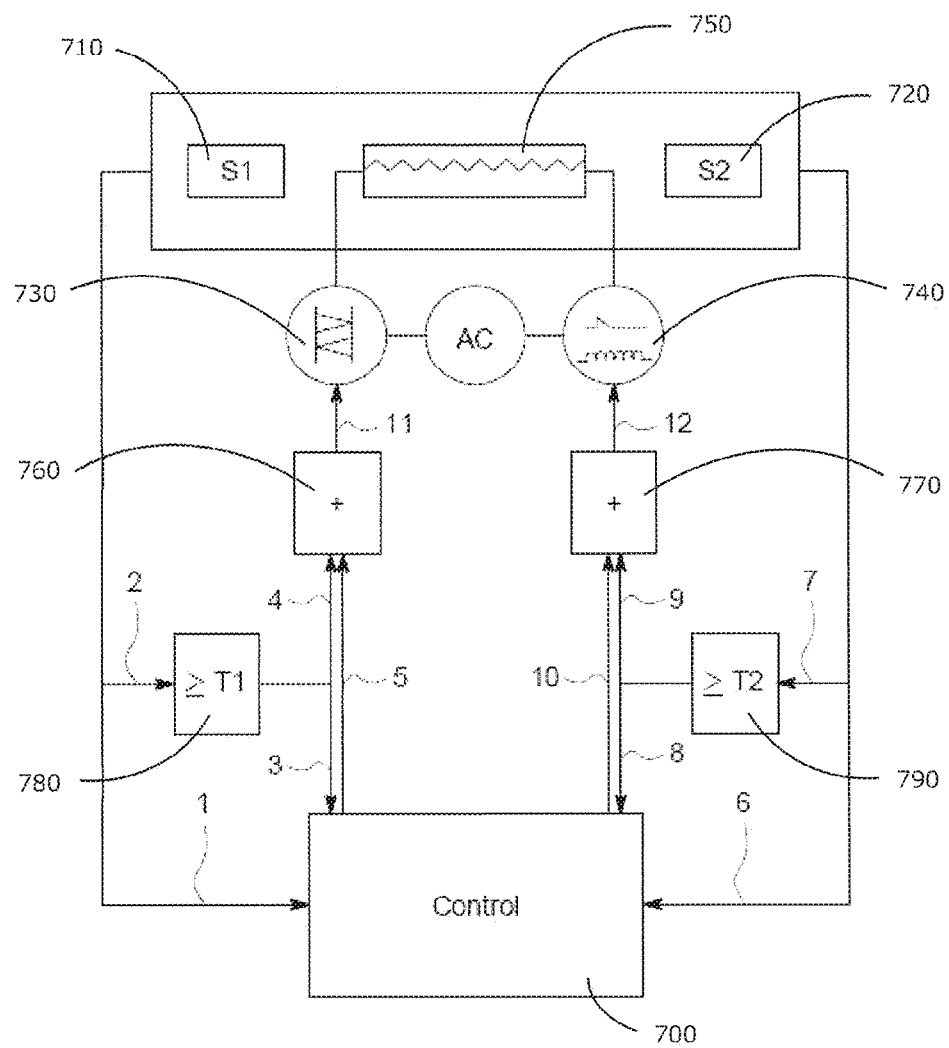
FIG. 17 is a schematic diagram of one form of electronic safety system to help prevent overheating of the apparatus.

In one form, as shown in FIG. 17, the control system may comprise the control unit 700 (as described above) and a first electronic protection system or circuit connected to the control unit 700. The first electronic protection circuit may comprise: a first temperature sensor 710; a first comparator circuit 780; and a first switching member 730. The first sensor 710 is configured to measure the temperature of the heating element 750 and provide first temperature sensor outputs to the first comparator circuit 780. The first comparator circuit 780 is a circuit (such as an op-amp) within the first electronic protection circuit that is configured to compare the first temperature sensor output to a first predetermined temperature threshold T1 to determine whether the heating element 750 is too hot, and to maintain or disable power to the heating element 750 depending on the output from the first sensor 710 and the determination of the heating element temperature. If the heating element temperature sensed by the first temperature sensor 710 lies below a first predetermined threshold T1, the first comparator circuit 780 will not cause the first switching member 710 to disable power to the heating element 750. Conversely, if the first comparator circuit determines that the first temperature sensor output exceeds the first predetermined threshold T1, the first comparator circuit 780 sends a signal 4, such as a DISABLE signal, to the first switching member to disable power to the heating element.

In one form, the first comparator circuit 780 may be configured to provide feedback to the control unit 700 by signaling 3 to the control unit 700 when a DISABLE signal 4 has been sent to the first switching member 730, or signaling 3 to the control unit 700 when no DISABLE signal 4 has been sent to the first switching member 730.

Additionally or alternatively, the control unit 700 may be configured to cause the first switching member 730 to disable power to the heating element 750 when the heating element 750 exceeds a first predetermined programmed temperature threshold, which is programmed into the control unit using software. In this form, the first electronic protection circuit is configured to provide feedback to the control unit 700 via electronic signals 1, 3. For example, the first temperature sensor 710 may be configured to provide sensed temperature outputs as feedback signals 1 to the control unit 700. The control unit 700 is programmed to receive the sensor output and determine if the heating element temperature is below the first programmed temperature threshold. If the control unit 700 determines that the sensed temperature exceeds the first programmed temperature threshold, the control unit 700 may send a signal 5 to the first switching member 730 to disable power to the heating element 750. For example, when the sensed heating element temperature exceeds the first programmed temperature threshold, the control unit 700 may send an electronic DISABLE signal 5 to the first switching member 730 to cause the first switching member 730 to disable power to the heating element 750. In this form, the first programmed predetermined temperature threshold may be different to, the same as, or similar to, the first predetermined threshold T1 of the first comparator circuit.

In one form, the first electronic protection circuit may comprise a logic gate 760 and signals 4, 5 from the first comparator circuit 780 and the control unit 700 may be sent to the logic gate 760. If both signals 4, 5 indicate that the heating element is at a desired operating temperature, the logic gate may signal 11 to the first switching member 730 to maintain power to the heating element 750. Conversely, if either signal 4, 5 indicates that the heating element 750 is too hot, the logic gate 760 will signal 11 to the first switching member to disable power to the heating element 750.

In this way, the control system also provides a secondary or back up protection mechanism to disable power to the heating element if the first electronic protection circuit does not cause the first switching member to disable power to the heating element.

In addition to the first electronic protection system or circuit, as shown in FIG. 17, the control system may comprise the control unit (as described above) and a second electronic protection circuit connected to the control unit. In this form, as above, the control system may be configured to control the operation of the second electronic protection circuit by sending electronic signals to one or more components of the second electronic protection circuit. One or more components of the second electronic protection circuit may also be configured to provide feedback to the control unit via electronic signals. For example, the second electronic protection circuit may comprise: a second temperature sensor 720; a second comparator circuit 790; and a second switching member 740. In this form, the second sensor 720 is configured to measure the temperature of the heating element 750 and provide a second temperature sensor output to the second comparator circuit 790. The second comparator circuit 790 is a circuit (such as an op-amp) within the second electronic protection circuit that is configured to compare the second temperature sensor output to a second predetermined temperature threshold T2 to determine whether the heating element 750 is too hot, and to maintain or disable power to the heating element 750 depending on the output from the second sensor 720 and the determination of the heating element temperature. If the sensed heating element temperature lies below the second predetermined temperature threshold T2, the second comparator circuit 790 will not cause the second switching member 720 to disable power to the heating element 750. Conversely, if the second comparator circuit 790 determines that the second temperature sensor output exceeds the second predetermined temperature threshold T2, the second comparator circuit 790 sends a signal 9, such as a DISABLE signal, to the second switching member 740 to disable power to the heating element.

The second switching member 740 may comprise a moveable switch, such as a mechanical isolation switch, configured to move from a first, connecting position to a second, disconnecting position to provide a physical disconnection of power to the heating element 750 by physically breaking the electronic circuit to the heating element 750 if the sensed temperature of the heating element 750 is too high.

In one form, the second comparator circuit 790 may be configured to provide feedback to the control unit 700 by signaling 8 to the control unit 700 when a DISABLE signal 9 has been sent to the second switching member 740, or signaling 8 to the control unit 700 when no DISABLE signal 9 has been sent to the second switching member 740.

The control unit may also be configured to cause the second switching member to disable power to the heating element when the heating element exceeds a second predetermined programmed temperature threshold, which is programmed into the control unit using software. In this form, the second electronic protection circuit is configured to provide feedback to the control unit 700 via electronic signals 6, 8. For example, the second temperature sensor 720 may be configured to provide sensed temperature outputs as feedback signals 6 to the control unit. The control unit 700 is programmed to receive the sensor output and determine if the heating element temperature is below the second programmed temperature threshold. If the control unit 700 determines that the sensed temperature exceeds the second programmed temperature threshold, the control unit 700 may send a signal 10 to the second switching member 740 to disable power to the heating element 750. For example, when the sensed heating element temperature exceeds the second programmed temperature threshold, the control unit 700 may send an electronic DISABLE signal 10 to the second switching member 740 to cause the second switching member 740 to disable power to the heating element 750. In this form, the second predetermined software threshold may be different to, the same as, or similar to, the second predetermined threshold T2 of the second comparator circuit. The second predetermined threshold temperature T2 may be equal to or higher than the first predetermined threshold temperature T1.

In one form, the second electronic protection circuit may comprise a logic gate 770. Signals 9, 10 from the second comparator circuit 790 and the control unit 700 may be sent to the logic gate 770. If both signals 9, 10 indicate that the heating element 750 is at a desired operating temperature, the logic gate 770 may signal 12 to the second switching member 740 to maintain power to the heating element 750. Conversely, if either signal 9, 10 indicates that the heating element 750 is too hot, the logic gate 770 will signal 12 to the second switching member 740 to disable power to the heating element 750.

In this arrangement, the control system acts as a secondary or back up protection mechanism configured to disable power to the heating element 750 if the second electronic protection circuit fails to cause the second switching member 740 to disable power to the heating element 750.

In another form, the control unit 700 may be configured to disable power to the heating element 750 via both the first and second switching members 730, 740 if the sensed temperature of the heating element 750 exceeds a predetermined temperature threshold (the sensed temperature being determined from the first 710 and/or second 720 sensor). For example, when the sensed temperature of the heating element 750, as measured by the first 710 and/or second sensor 720, exceeds a predetermined threshold, the control unit 700 may signal to both the first switching member 730 and to the second switching member 740 to disable power to the heating element 750.

In one form, at least the first switching member 710 and optionally the second switching member 720 may be reset when the first electronic protection circuit identifies from the first sensor outputs that the heating element temperature has dropped below T1.

In one form, the second electronic protection circuit may only be resettable by power cycling the apparatus. For example, if the second electronic protection circuit is reset, the second switching member, which is preferably a mechanical isolation switch, may move from a disconnecting position to a connecting position to reinstate power to the heating element.

In a preferred form, the second switching member, which may be a mechanical isolation switch, is in a disconnecting position when the breathing assistance apparatus is not providing therapy, and is only moved to a connecting position by the control unit when the breathing assistance apparatus is providing therapy. Having the mechanical isolation switch in a disconnecting position prevents damage to the electronics that may otherwise be caused by any power surges that occur when the device is not providing therapy.

The mechanical isolation switch may be any suitable form of switch, such as an electronically controlled switch configured to provide a mechanical connection and disconnection of power to the heating element by moving from a first position to a second position. For example, the mechanical isolation switch may be a relay.

The electronic switching member configured to electronically disconnect power to the heating element may also be any suitable form of electronic switch to connect and disconnect power to the heating element, such as a triac, metal-oxide-semiconductor field-effect transistor (MOSFET), or insulated-gate bipolar transistor (IGBT) for example.

In one form, the control system of the apparatus 100 may comprise only the first electronic protection circuit or only the second electronic protection circuit, as described above, or the control system may comprise both the first and second electronic protection circuits described above, as shown in FIG. 17.

In one form, the programmable control unit may be configured to monitor outputs (the sensed temperature readings) of the first and second temperature sensors and to independently calculate the sensed temperature of the heating element based on those outputs. In one form, this calculation is made by averaging the temperature outputs from the first and second temperature sensors. The resulting calculation is referred to herein as the control unit sensed temperature. In another form, the control unit may calculate the control unit sensed temperature by utilizing peak temperature sensing or other suitable signal processing techniques.

In one form, when the control unit sensed temperature exceeds a predetermined programmed temperature threshold, the control unit may cause the first and/or second switching members of the first and second electronic protection circuits respectively to disable power to the heating element. The predetermined programmed temperature threshold may be below, equal to or higher than the first predetermined temperature threshold T1, or below, equal to or higher than the second predetermined temperature threshold T2.

In one form, where the control system comprises only a first electronic protection circuit comprising only a first switching member, the control unit may be configured to trigger the first switching member to disable power to the heating element if the control unit sensed temperature remains at or above a predetermined threshold temperature for a predetermined period of time. Where the control system comprises first and second electronic protection circuits with first and second switching members, the control unit may be programmed to trigger one or both switching members to disable power to the heating element if the control unit sensed temperature remains at or above a predetermined threshold temperature for a predetermined period of time. For example, the control unit may trigger the mechanical isolation switch to disable power to the heating element.

In one form, the control unit may be programmed to identify the difference in outputs between the first and second temperature sensors and to cause one or both switching members to disable power to the heating element when the control system identifies that the outputs of the first and second sensors differ by a predetermined programmed threshold. If the control unit detects a difference in the outputs of the first and second temperature sensors, then it is possible that at least one of the temperature sensors has failed, and that either one or both of the first and second electronic protection circuits may not reliably disable power to the heater plate.

In one form, as shown in FIG. 7, the apparatus 100 may be configured to use air flow to help cool the electronics in the base 330. For example, a venturi channel 431 may be provided between a bottom surface of the floor 434 of the sub-housing 430 and a top surface of the floor 234 of the lower housing 230. The channel may provide an inlet flow path for air flowing from an inlet toward the blower. The air inlet may be located on a real wall, side wall or front wall of the apparatus 100. Where the floor 234 of the lower housing is substantially thin, the flow of air along the channel 431 may cool the area beneath the floor 234. In other words, by configuring the apparatus to direct air flow through the channel 431, it may be possible to help cool electronic components held beneath the floor of the lower housing.

The base 330 may be configured to provide a substantially stable platform on which the upper 130 and lower 230 housings may be supported. It may be particularly important for the apparatus 100 to remain stable, such as when a user is loading or unloading the humidification chamber, to help prevent water leaks and protect the electronics within the apparatus 100. To help the stability of the apparatus 100, the apparatus 100 may comprise at least two feet 500 located on opposing sides of the apparatus 100 and configured to provide the apparatus 100 with a stable base. For example, the feet 500 may be substantially elongate and may extend along at least a portion of opposing sides of the bottom surface of the apparatus 100. Preferably, bottom surfaces of the feet 500 are at least partially tacky. For example, the bottom surfaces of the feet 500 may comprise rubber to increase friction between the feet 500 and a supporting surface on which the apparatus 100 is located during use.

Figure 18:
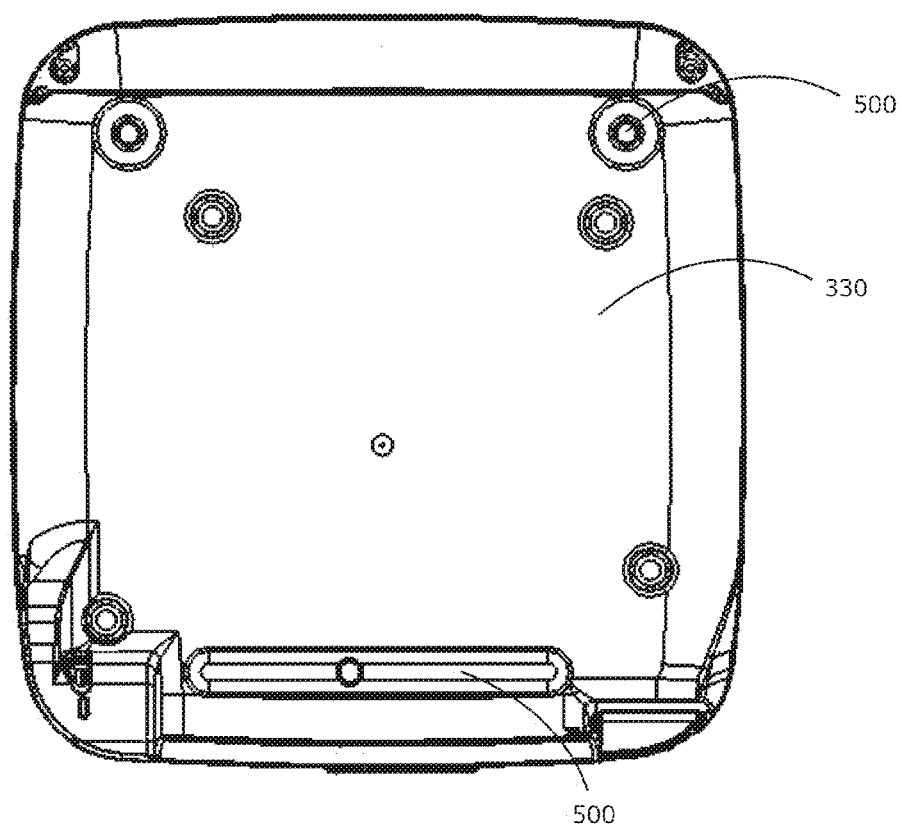
FIG. 18 is a bottom view of the bottom surface of one form of base and showing one form of foot arrangement.

In one form, the apparatus 100 comprises three feet 500 to provide increased stability. The three feet 500 may be substantially evenly or unevenly spaced on the bottom surface of the apparatus 100. In one form, as shown in FIG. 18, the apparatus 100 may comprise an elongated foot 500a projecting from the bottom surface of the apparatus and extending in a direction from one side of the apparatus to the other. The apparatus may also comprise two smaller feet spaced apart from the elongate foot. For example, one foot (such as a small round or otherwise shaped foot) may be located at or near each front corner of the apparatus and a third elongate foot may be located near the rear of the apparatus and be oriented to extend from one side of the apparatus to the other, as shown in FIG. 18. Spaces provided between the feet 500 allow for air to flow freely beneath the apparatus 100, which may help to cool the base 330 of the apparatus where the electronics may be held. In one form, the feet 500 project from the bottom surface of the base 330 of the apparatus 100.

To attach the parts of the apparatus 100 together, the upper and lower housings 130, 230 may be formed separately and may then be connected together in any suitable configuration to form the body 110 of the apparatus 100. Preferably, the upper housing 130, including the inner and outer walls 131, 132 and lower wall 134, is formed as a single part. Additionally or alternatively, the lower housing 230, including the inner and outer walls 231, 232 and lower wall 234, is formed as a single part. The upper housing 130 is located above the lower housing 230 and is attached to the lower housing 230, which may in turn be attached to the base 330 to form the body 110 of the apparatus 100. A sub-housing 430 may be located within the apparatus and between the upper housing 130 and lower housing 230.

In one form, the upper housing 130, lower housing 230, and base 330 are connected together by fasteners that engage with each of these three parts 130, 230, and 330 of the apparatus 100. For example, fasteners in the form of screws, bolts, or the like may extend through substantially aligned attachment apertures in the upper housing 130, lower housing 230 and base 330 to attach all three parts together. The aligned attachment apertures may be placed at any suitable location. In one form, the body 110 of the apparatus 100 comprises four outer corners and the aligned attachment apertures are located near the outer corners. A screw or bolt or other suitable fastener may be inserted into the aligned attachment apertures to attach the upper housing 130, lower housing 230, and base 330 together. In one form, the sub-housing 430 may also comprise one or more attachment apertures that align with the attachment apertures of the upper and lower housings and base so that fasteners can be used to attach all of the components 130, 230, 330, 430 together.

In this configuration, a gap 150 may be formed between a lower peripheral edge of the outer wall of the upper housing 130 and an upper edge of the lower housing 230. Sometimes, the gap 150 may be of uneven width along its length as the gap extends around the body 110 of the apparatus 100. The uneven width of the gap 150 may be aesthetically unattractive. Therefore, to provide a gap 150 having a substantially constant width around the body 110 of the apparatus 100, the body 110 of the apparatus may comprise at least two spacers, which may be in the form of protrusions 160, or the like, of substantially equal height that extend into the gap 150 to space the upper housing 130 and lower housing 230 at an equal distance apart, as shown in FIGS. 19a and 19b. In one form, the spacers 160 may be located on an upper edge of the lower housing 230. In another form, the spacers 160 may be located on a lower edge of the upper housing 130, particularly on the lower edge of an outer wall of the upper housing 130. The spacers 160 may be of any suitable height, such as between 3 mm to 8 mm for example. In a preferred form, the spacers 160 are 5 mm high.

Figure 20:
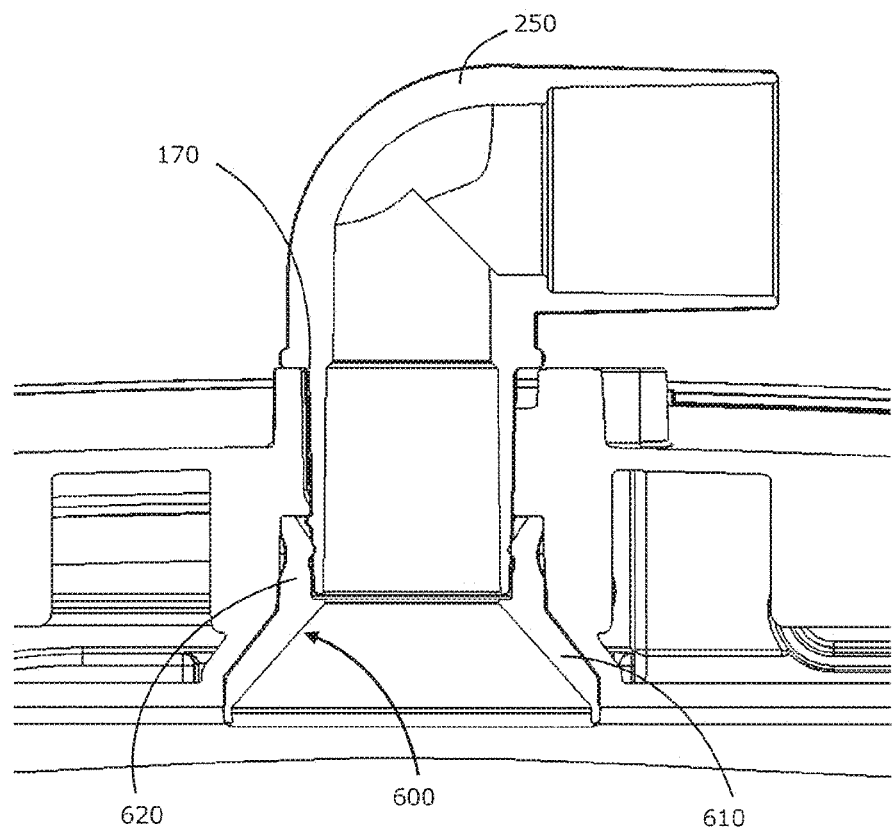
FIG. 20 is a plan view of a portion of one form of apparatus of the invention showing a portion of a rear wall structure of the apparatus and one form of outlet seal arrangement that may be used with the apparatus.
Figure 21:
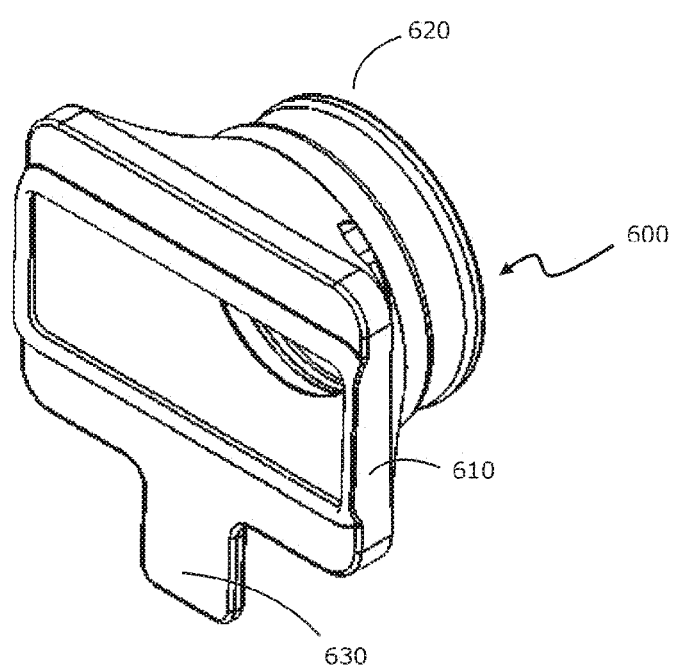
FIG. 21 is a perspective view of one form of an outlet seal that may connect to an outlet of a breathing assistance apparatus.

In one form, as shown in FIGS. 20 and 21, the breathing assistance apparatus 100 may be configured to comprise an outlet seal 600 that is configured to help create a sterile environment at the connection between an air outlet 170 of the apparatus and the breathing tube 200. In this configuration, it may be easier to refurbish the apparatus 100 between uses by different patients.

The outlet seal 600 is configured to be at least partially located within the air outlet 170 of the apparatus 100. An air flow path is provided between the body 610 and connection port 620 so that air may flow through the outlet seal in the air outlet 170 and into the breathing tube 200.

The air outlet 170 and outlet seal 600 may be shaped to substantially complement each other so that outer surfaces of the outlet seal 600 may substantially seal against inner surfaces of the air outlet 170 when the outlet seal 600 is placed within the air outlet 170.

In one form, the air outlet 170 is located within the rear wall structure of the apparatus. However, in other forms, the air outlet may be located in a side wall of front wall of the apparatus. A first portion of the air outlet 170 may comprise a non-circular interior surface to help prevent the outlet seal from rotating within the air outlet. In one form, the non-circular interior surface may be a quadrilateral surface, such as a rectangular surface, as shown in FIG. 20. A second portion of the air outlet 170 may comprise a substantially circular interior surface configured to receive an end of a breathing tube 200 having a substantially circular peripheral surface. The first portion of the air outlet is typically open to the interior wall of the apparatus 100 and the second portion of the air outlet is typically open to the exterior wall of the apparatus 100.

In one form, the outlet seal 600 comprises a body 610 and a connection port 620 that projects from the body 610. The connection port 620 of the outlet seal 600 may comprise a substantially circular interior surface to envelop and substantially seal against an end of a breathing tube 200 having a substantially circular peripheral surface. Optionally, the exterior surface of the connection port 620 may also be substantially circular and may be configured to seal against a substantially circular interior surface of the air outlet 170.

In one form, the body 610 of the outlet seal 600 may comprise a non-circular exterior surface configured to substantially seal against or engage with the first portion of the air outlet. For example, where the first portion of the air outlet 170 comprises a rectangular interior surface, the exterior surface of the outlet seal body 610 may also be rectangular and may be configured to fit snugly within the first portion of the air outlet 170. In this configuration, it is not possible for the outlet seal 600 to rotate within the air outlet 170.

The outlet seal 600 may be placed within the first portion of the air outlet 170, such as by pushing the connection port 620 and at least part of the body 610 of the outlet seal into the first portion of the air outlet 170.

Preferably, the outlet seal 600 is configured so that the inner surface of the connection port 620 has a diameter substantially the same as that of the inner surface of the second portion of the air outlet 170. In this arrangement, an end of a breathing tube 200 (or an adapter 250 that connects to a breathing tube) may be pushed, from the exterior of the apparatus 100, into the second portion of the air outlet 170 and into the connection port 620 of the outlet seal.

In one form, a stop, such as a flange or one or more projections, may be located between the interior surface of the connection port 620 and the body 610 of the outlet seal. The stop may be configured to prevent the end of the breathing tube 200 or adapter 250 from extending into the body 610 of the outlet seal.

In one form, the outlet seal 600 and air outlet 170 may be configured so that substantially the whole of the outlet seal 600 is located within the air outlet 170. In another form, the body 610 of the outlet seal may comprise a depth control member that extends from a side of the outlet seal 610 and that is configured to prevent the whole of the outlet seal 600 from being pushed into the air outlet 170. For example, the depth control member may be a flange or other form of projection that extends from a side of the outlet seal body 610 and that abuts the interior surface of the wall within which the air outlet is located to prevent the outlet seal from being pushed further into the air outlet.

In one form, the outlet seal comprises a gripping region to enable a user to easily grip the seal and extract the seal from the air outlet. The gripping region is typically located on the body of the outlet seal. In one form, the gripping region comprises a tab that projects from the body and that is configured to abut the interior surface of the wall within which the air outlet and outlet seal are located. In this arrangement, the tab 630 is easily accessible when the seal is placed within the air outlet 170. To extract the outlet seal

600 from the air outlet 170, a user simply needs to pull on the tab 630 with suitable force. The tab may be used as both a gripping region and a depth control member.

A significant advantage of the apparatus 100 is that it may be manufactured from the top down. For example, the apparatus 100 may begin to be constructed by placing the lid 120 upside down and then locating the upper housing 130 on the lid 120. The lower housing 230 can then be connected to the upper housing 130 and then the base 330 may be connected to the lower housing 230. The face plate 141 may then be attached to the assembled unit. By building the apparatus 100 from the top down, the apparatus 100 may be constructed almost entirely from one position. It is therefore possible to reduce handling and manufacturing time.

The upper housing 130 of the apparatus may be manufactured as a single part by injection moulding, with the gates in two opposite corners on the top edge or upper surface 133 of the housing, from which the plastic can reach both the inner and outer walls without overly stressing the moulding tools. As a result of this form of manufacture, it is possible to provide the upper housing with an outer wall structure in which the inner and outer walls are integrally formed to avoid a join between the walls. It is desirable to avoid placing a join between the inner and outer walls because water and other liquids may otherwise enter into the join and seep between the inner and outer walls to access electronic components within the apparatus. The lower housing may also be injection moulded in the same manner.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

What is claimed is:

1. A breathing assistance apparatus for the delivery of breathing gas to a user, the apparatus comprising:
    a body and a lid, the body comprising at least one housing, the at least one housing comprising three inner walls and three outer walls, wherein each of the three outer walls is substantially adjacent to and spaced apart from a respective one of the three inner walls;
    an upper surface spanning between upper edges of the three outer walls and the three inner walls, wherein the three outer walls, the three inner walls, and the upper surface are integrally formed as a single piece of material,
    wherein the three inner walls form an enclosure for a humidification chamber,
    wherein the lid covers the enclosure,
    wherein the at least one housing further comprises a fourth inner wall and a face plate, the face plate located substantially adjacent to and spaced apart from the fourth inner wall to form a fourth outer wall of the at least one housing;
    a compressible facing comprising a first portion located between the face plate and the fourth inner wall; and
    a display located between the face plate and the fourth inner wall.

2. The apparatus of claim 1, further comprising a heating element located in an aperture of a lower wall of the enclosure.

3. The apparatus of claim 1, further comprising a printed circuit board (PCB) located between the face plate and the fourth inner wall.

4. The apparatus of claim 3, further comprising two or more sensors located on one face of the PCB, and wherein the apparatus further comprises an interior wall comprising two or more apertures that substantially align with the two or more sensors, such that the two or more sensors project through the two or more apertures in the interior wall and into an air flow path located within the apparatus, by pushing the PCB against the interior wall.

5. The apparatus of claim 4, wherein the two or more apertures comprise soft seals around walls of the two or more apertures and wherein the soft seals are co-molded to the interior wall of the apparatus.

6. The apparatus of claim 1, further comprising a printed circuit board (PCB) located between the face plate and the fourth inner wall, wherein the first portion of the compressible facing is located between the PCB and the face plate.

7. The apparatus of claim 6, wherein the compressible facing comprises a second portion located between the PCB and interior structures of the at least one housing to provide damping to both faces of the PCB.

8. The apparatus of claim 6, wherein the PCB comprises one or more apertures through which arms of the compressible facing project so that the PCB is supported by the compressible facing.

9. The apparatus of claim 6, wherein the first portion of the compressible facing comprises one or more apertures that substantially align with LED lit components located on the PCB.

10. The apparatus of claim 9, wherein substantially a whole of the face plate is tinted.

11. The apparatus of claim 1, wherein the compressible facing is silicone or rubber.

12. The apparatus of claim 1, wherein the at least one housing comprises an upper housing, a lower housing and a base, wherein the lower housing is connected to both the upper housing and the base, and wherein the face plate forms the fourth outer wall, wherein the fourth outer wall is an outer wall for at least the upper housing and the lower housing.

13. The apparatus of claim 12, further comprising a sub-housing between the upper housing and the lower housing.

14. The apparatus of claim 12, wherein the base comprises one or more drainage channels.

15. The apparatus of claim 14, wherein the one or more drainage channels are connected to one or more outlets.

16. The apparatus of claim 15, wherein the one or more drainage channels are located along one or more sides of the apparatus.

17. The apparatus of claim 15, wherein the one or more drainage channels terminate at the one or more outlets.

18. The apparatus of claim 12, wherein the first portion of compressible facing is located on a first side of the display and a second side of the display, the second side of the display opposing the first side of the display.

19. The apparatus of claim 18, further comprising at least one user input, wherein the first portion of the compressible facing surrounds the at least one user input.

20. The apparatus of claim 19, wherein the at least one user input comprises a first user input positioned on the first side of the display and a second user input located on the second side of the display.

\* \* \* \* \*